US006799629B1

(12) United States Patent
Cong et al.

(10) Patent No.: US 6,799,629 B1
(45) Date of Patent: Oct. 5, 2004

(54) COOLING APPARATUS FOR A MULTIPLEXED CAPILLARY ELECTROPHORESIS SYSTEM

(75) Inventors: Peijun Cong, San Jose, CA (US); Robert D. Doolen, Sunnyvale, CA (US); Tony N. Wheeler, Santa Clara, CA (US)

(73) Assignee: Symyx Technologies, Inc., Santa Clara, CA (US)

( * ) Notice: Subject to any disclaimer, the term of this patent is extended or adjusted under 35 U.S.C. 154(b) by 554 days.

(21) Appl. No.: 09/852,159

(22) Filed: May 9, 2001

Related U.S. Application Data

(63) Continuation-in-part of application No. 09/621,890, filed on Jul. 20, 2000, now Pat. No. 6,544,396.

(51) Int. Cl.[7] .............................. F28F 5/00; F28F 3/12; F28F 3/14; F28F 7/00
(52) U.S. Cl. ..................... 165/86; 165/168; 165/170; 165/76; 165/11.1
(58) Field of Search ........................... 165/86, 11.1, 168, 165/170, 76; 204/601, 602, 603

(56) References Cited

U.S. PATENT DOCUMENTS

| | | | | |
|---|---|---|---|---|
| 3,655,980 | A | | 4/1972 | Bossen .................. 250/83.3 D |
| 4,172,227 | A | | 10/1979 | Tyrer et al. ............. 250/461 B |
| 4,177,858 | A | * | 12/1979 | Daman et al. ............. 165/11.1 |
| 4,375,163 | A | | 3/1983 | Yang ....................... 73/61.1 C |
| 4,520,305 | A | * | 5/1985 | Cauchy ...................... 322/2 R |
| 4,576,477 | A | | 3/1986 | Corbet et al. ................. 356/39 |
| 4,618,769 | A | | 10/1986 | Johnson et al. ............. 250/338 |
| 4,747,686 | A | | 5/1988 | Sato ............................. 356/72 |
| 4,854,700 | A | * | 8/1989 | Cutie et al. ................... 356/72 |
| 5,003,488 | A | | 3/1991 | Hardy ......................... 364/509 |
| 5,045,172 | A | | 9/1991 | Guzman ................. 204/299 R |
| 5,066,382 | A | | 11/1991 | Weinberger et al. .... 204/299 R |
| 5,085,757 | A | * | 2/1992 | Karger et al. ............... 204/603 |
| 5,124,020 | A | * | 6/1992 | Wang ......................... 204/452 |
| 5,198,091 | A | * | 3/1993 | Burolla et al. ............. 204/601 |
| 5,239,360 | A | | 8/1993 | Moring et al. .............. 356/344 |
| 5,274,240 | A | | 12/1993 | Mathies et al. .......... 250/458.1 |

(List continued on next page.)

FOREIGN PATENT DOCUMENTS

WO    99/42819    8/1999

OTHER PUBLICATIONS

Culbertson, C.T. et al., "Lowering The UV Absorbance Detection Limit In Capillary Zone Electrophoresis Using a Single Linear Photodiode Array Detector", *Anal. Chem.*, vol. 70, pp. 2629–2638, Jul. 1998.

(List continued on next page.)

*Primary Examiner*—Henry Bennett
*Assistant Examiner*—Tho V Duong
(74) *Attorney, Agent, or Firm*—Senniger Powers

(57) ABSTRACT

Apparatus for cooling a bundle of capillary tubes to prevent overheating of the tubes during a parallel capillary electrophoresis procedure. The apparatus includes a jacket of thermally conductive solid material comprising mating jacket members movable between an open position in which the jacket members are separated to allow placement of the bundle in the jacket and a closed position in which the jacket members are mated together and the bundle is disposed inside the jacket in thermally conductive relation with the jacket. Window openings in the mating jacket members define a window to permit the passage of light through the window and the capillary tubes of the bundle at the location of the window.

29 Claims, 20 Drawing Sheets

U.S. PATENT DOCUMENTS

| | | |
|---|---|---|
| 5,303,021 A | 4/1994 | Kita ............................. 356/72 |
| 5,312,535 A | 5/1994 | Waska et al. ............ 204/299 R |
| 5,324,401 A | 6/1994 | Yeung et al. ............. 204/180.1 |
| 5,413,686 A | 5/1995 | Klein et al. .............. 204/299 R |
| 5,439,578 A | 8/1995 | Dovichi et al. .......... 204/299 R |
| 5,488,240 A | 1/1996 | Hlousek et al. ......... 250/231.16 |
| 5,582,705 A | 12/1996 | Yeung et al. ................. 204/603 |
| 5,611,903 A | 3/1997 | Janssens et al. ............. 204/454 |
| 5,695,626 A | 12/1997 | Yeung et al. ................ 204/605 |
| 5,730,850 A | 3/1998 | Kambara et al. ............ 204/603 |
| 5,741,411 A | 4/1998 | Yeung et al. ................ 204/452 |
| 5,900,934 A | 5/1999 | Gilby et al. ................. 356/344 |

OTHER PUBLICATIONS

Gong, Xiaoyi et al., "An Absorption Detection Approach for Multiplexed Capillary Electrophresis Using a Linear Photodiode Array", *Analytical Chemistry*, pp. A–H, 1999.

Product Catalog, "Swagelok® BMS Series Bellows Sealed Metering Valves", Nupro Company, Feb. 1997.

Product Catalog, "Swagelok® Ultra–High–Purity Diaphragm Valve; DA Series", Nupro Company, May 1998.

Product Bulletin 640/641, "Electronic Pressure Controllers, 640 Series", MKS Instruments, Inc., Jul. 1995.

* cited by examiner

COOLING APPARATUS FOR A MULTIPLEXED CAPILLARY ELECTROPHORESIS SYSTEM

CROSS-REFERENCE TO RELATED APPLICATION

This application is a continuation-in-part of U.S. application Ser. No. 09/621,890, filed Jul. 20, 2000 now U.S. Pat. No. 6,544,396, by Peijun Cong and Robert Doolen, titled "Multiplexed Capillary Electrophoresis System for Chiral Separation", which is incorporated by reference herein for all purposes.

BACKGROUND OF THE INVENTION

This invention is generally in the field of capillary electrophoresis, and relates particularly to apparatus and method for cooling the capillaries of a multiplexed or "parallel" capillary electrophoresis system.

Capillary electrophoresis (CE) is a chemical separation technique involving the use of one or more capillary tubes. Parallel CE, a recently developed technique using many parallel capillary tubes, is growing in popularity since this technology allows multiple samples to be analyzed quickly and efficiently. This is particularly advantageous in combinatorial chemistry where many hundreds and even thousands of samples are analyzed over a short period of time. Parallel CE involves the use of a "bundle" of capillary tubes, e.g., 24, 48, 96 or other number of such tubes. A chemical sample to be analyzed is loaded in each tube, and a high voltage is applied to the tube, causing the components of the sample to migrate in the tube at different speeds, thereby causing separation of the components which can then be analyzed by conventional light absorption or other techniques. Reference may be made to the following patents and publications for a more detailed description of CE, including parallel CE, and various analytical techniques used in CE: U.S. Pat. Nos. 5,900,934, 5,324,401, 5,312,535, 5,303,021, 5,239,360; C.Culbertson et al., *Analytical Chemistry*, 70, 2629–2638 (1998); and X. Gong et al., *Analytical Chemistry*, 71, 4989–4996 (1999). None of these publications disclose the use of parallel CE to achieve chiral separation.

The electrical current passing through the parallel capillary tubes of a CE system can generate a substantial amount of heat, particularly where high voltages and electrical currents are used to achieve the separation of the samples, as during a chiral separation process using chiral buffers, or when CE is run in a micellar electrokinetic chromatography (MEKC) mode where the current is high and the temperature rise in the capillary tubes due to Joule heating can be large. If not dissipated, this heat can cause the formation of bubbles in the samples, sparking, and other undesirable results having an adverse affect on separation and analysis. Therefore, there is a need for a system for effectively cooling such tubes.

SUMMARY OF THE INVENTION

Among the several objects of this invention may be noted the provision of cooling apparatus and a related method useful for preventing overheating of the capillary tubes and contents thereof when CE is run in a mode (e.g., an MEKC mode) generating substantial heat; the provision of such apparatus and method having no adverse affect on the separation and/or analytical process; the provision of such cooling apparatus which is adjustable to various cooling temperatures; the provision of such cooling apparatus which can be configured to remove a desired amount of heat; the provision of such apparatus which is safe to use.

In general, this invention is directed to apparatus for cooling a bundle of capillary tubes to prevent overheating of the tubes during a parallel capillary electrophoresis procedure. The apparatus comprises a jacket of thermally conductive solid material comprising mating jacket members movable between an open position in which the jacket members are separated to allow placement of the bundle in the jacket and a closed position in which the jacket members are mated together and the bundle is disposed inside the jacket in thermally conductive relation with the jacket. Window openings in the mating jacket members define a window to permit the passage of light through the window and the capillary tubes of the bundle at the location of the window.

The present invention is also directed to cooling comprising inner and outer jackets. The inner jacket is of thermally conductive, electrically insulating solid material comprising mating inner jacket members movable between an open position in which the jacket members are separated to allow placement of the bundle in the jacket and a closed position in which the jacket members are mated together and the bundle is disposed inside the inner jacket in thermally conductive relation with the jacket. The outer jacket is of thermally conductive solid material comprising mating outer jacket members movable between an open position in which the jacket members are separated and a closed position in which the jacket members are mated together around the inner jacket and in thermally conductive relation therewith. The apparatus also includes a cushion of thermally conductive, cushioning material disposed inside the inner jacket for cushioning the bundle when the inner and outer jacket members are in the closed position. A window is provided through the mating inner and outer jacket members for permitting the passage of light through the window and the tubes of the bundle at the location of the window.

The present invention also involves a method of cooling a bundle of capillary tubes to prevent overheating of the tubes during a parallel capillary electrophoresis procedure. The method comprises positioning a longitudinal section of the bundle in an open cooling jacket of electrically insulating, thermally conductive solid material, and arranging the tubes of the longitudinal bundle section so that the tubes extend generally parallel and in side-by-side relation to one another in a generally planar array in the jacket. The jacket is then closed to enclose within the jacket said longitudinal section of the bundle from one end of the section to the other, said tubes of the longitudinal section being in thermal conductive relation with the jacket. The method also includes initiating a capillary electrophoresis procedure resulting in the generation of heat within the tubes of the bundle, the jacket functioning to cool said longitudinal section of the bundle to prevent overheating of the bundle.

Other objects and features will be in part apparent and in part pointed out hereinafter.

BRIEF DESCRIPTION OF THE DRAWINGS

Corresponding parts are designated by corresponding reference numbers throughout the several views of the drawings.

DETAILED DESCRIPTION OF THE PREFERRED EMBODIMENTS

Figure 1:
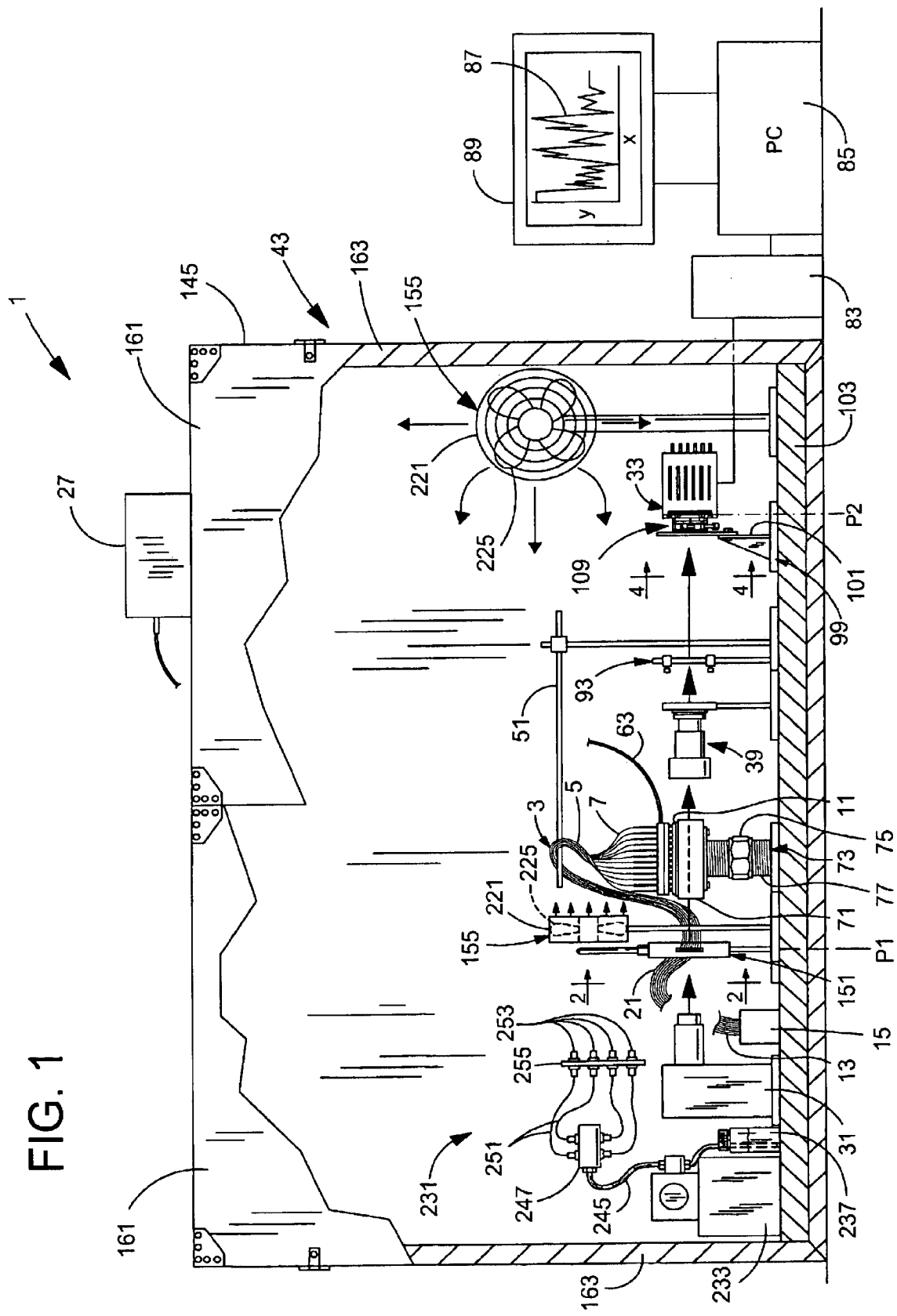
FIG. 1 is a schematic view of a capillary electrophoresis system with cooling apparatus for preventing overheating of the capillary tubes during a chiral separation process.
Figure 2:
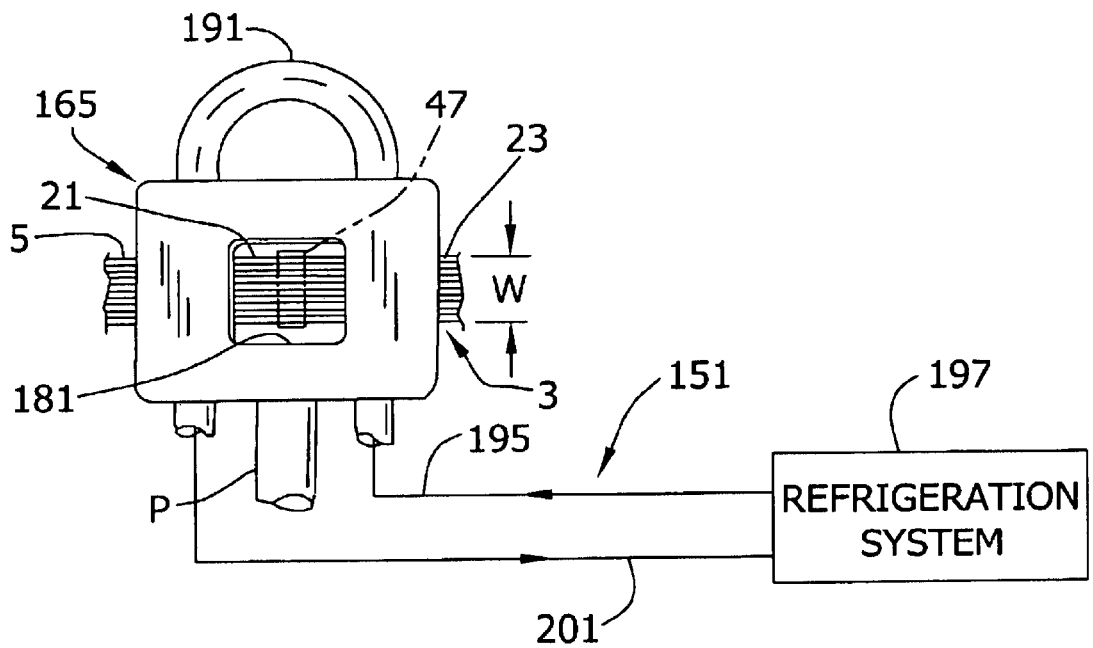
FIG. 2 is an enlarged view along lines 2—2 of FIG. 1 showing a conduction cooling device for cooling an array of closely spaced parallel capillary tubes.
Figure 10:
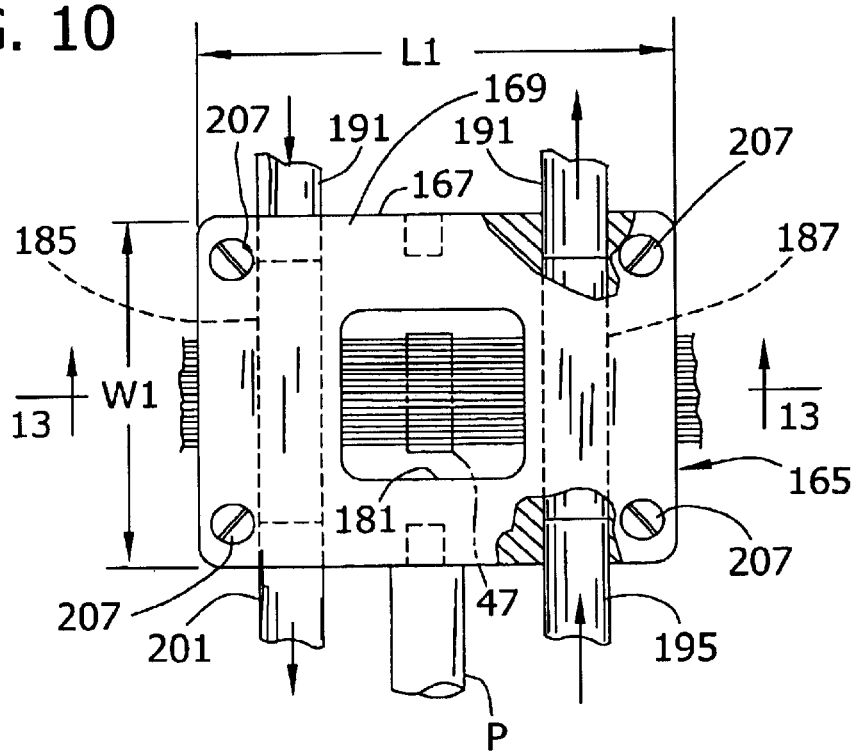
FIG. 10 is a front view of certain components of the cooling device of FIG. 2, including a cooling body.

Referring now to the drawings, FIG. 1 shows a multiplexed (parallel) capillary electrophoresis (CE) system, generally indicated at 1, for separating and analyzing the components of multiple chemical samples. The system comprises a bundle 3 of capillary tubes 5 having inlet end portions 7 spaced apart (e.g., spread out in a fanned formation) for loading of fluid samples to be analyzed from individual wells 9 (FIG. 3) in a microtiter plate 11 into the tubes, outlet end portions 13 for exit of the fluid samples from the tubes into a waste receptacle 15, and intermediate portions 21 between the inlet and outlet portions arranged in a generally planar, ribbon-like array 23 (FIG. 2) in which the intermediate portions extend side-by-side in closely spaced generally parallel relation in a first plane P1. The system also includes a power source 27 for applying a potential (voltage) difference between the inlet end portions 7 and the outlet end portions 13 to cause an electrical current to flow through the contents of the capillary tubes 5, a light source 31 for emitting light to pass through the closely spaced array 23 of intermediate portions 21 of the capillary tubes, and a photodetector generally designated 33 comprising a linear array 34 of photodetector elements (35 in FIGS. 8 and 9) in a second plane P2 generally parallel to the first plane P1 for receiving light passing through the planar array of intermediate portions of the capillary tubes. Light passing through the tubes 5 is imaged on the photodetector 33 by an imaging lens, generally designated 39. In accordance with this invention, the system also includes a cooling system, generally indicated at 43, for dissipating the large quantities of heat generated in the capillary tubes 5 and contents thereof during a high-heat separation process, such as a chiral separation process.

More specifically, the capillary bundle 3 may comprise a series of 96 capillary tubes 5, although this number may vary. Each tube 5 is of relatively small diameter (e.g., 50 microns ID; 150 microns OD) and of a suitable electrically nonconductive material, such as fused silica so that high voltages can be applied across tube without generating excessive heat. The tubes 5 may have a polyimide coating which is removed by a laser beam, for example, in an area extending across the planar array 23 of intermediate portions 21 of the capillary tubes, thereby forming what may be referred to as a detection window (47 in FIG. 2) which is transparent or translucent so that light from the light source 31 can pass through the walls of the tubes at this location. Alternatively, the tubes can be transparent or translucent along their entire lengths, in which case no coating removal is necessary. The bundle 3 is of any appropriate length (e.g., 10 cm–2 m). At the detection window 47 the bundle 3 has a width, designated W in FIG. 2, in a direction generally perpendicular to its length. As illustrated in FIG. 1, the bundle 3 may be supported above its inlet end portions 7 by a suitable support device 51. The capillary tubes 5 of the bundle 3 may be held in the aforementioned planar array 23 by any suitable means, such as by strips of adhesive tape (not shown) extending across the array on opposite sides of the detection window 47.

Figure 3:
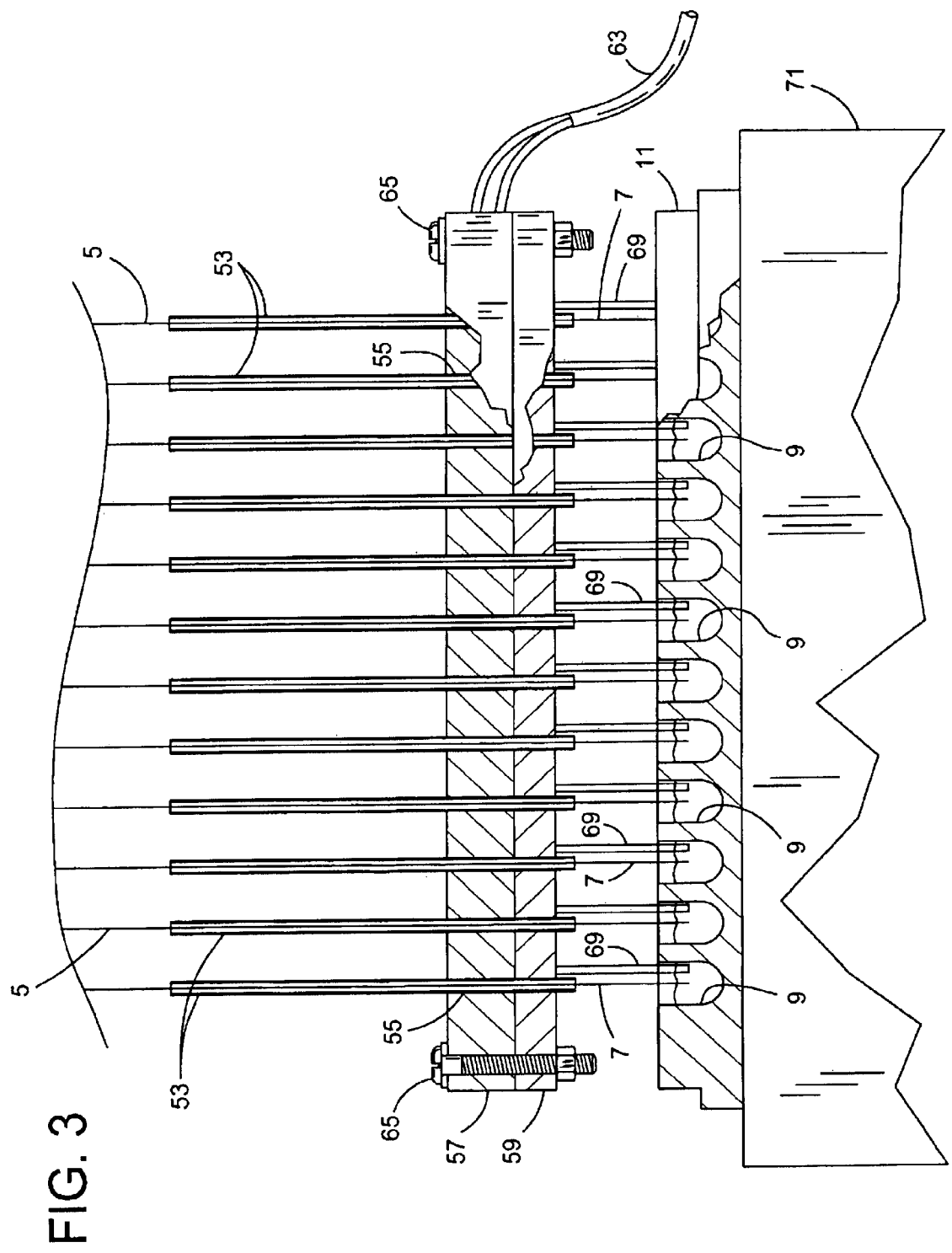
FIG. 3 is an enlarged sectional view of capillary tubes extending down through power plates into the wells of a microtiter plate.

Referring to FIG. 3, the inlet end portions 7 of the capillary tubes 5 extend through tubular sleeves 53 of electrical insulating material slidably received in holes 55 in a pair of upper and lower metal power plates 57, 59 connected to the power source 27 by suitable electrical cable 63. The two plates 57, 59 are secured together by fasteners 65. The inner end portions 7 of the capillary tubes 5 extend down beyond the sleeves 53 and into respective wells 9 in the microtiter plate 11 containing liquid samples of chemical compositions to be analyzed. Metal electrodes 69 are secured (e.g., brazed) to the bottom face of the lower power plate 59 and extend down into the wells 9 alongside the capillary tubes 5 for electrifying the contents of the wells when the power source 27 is activated. The power plates 57, 59 and electrodes 69 are preferably of copper or other suitable metal, and the lower plate 59 and electrodes are preferably gold plated to render them chemically inert or non-reactive. To effect chiral separation, substantially more (3–5 times more) current must be used than in non-chiral separations. For example, for a bundle of 96 capillary tubes, a total current of 750 milliamps at a voltage of 10,000–30,000 volts may be required to effect separation. A suitable power source for this application is Model 105-30R, available from Bertan High Voltage Corporation located in Hicksville, New York.

The microtiter plate 11 is supported by a thick insulating block 71 of dielectric material which is movable up and down relative to the power plates 57, 59 by a linear actuator generally designated 73. The actuator 73 is operated by rotating a nut 75 relative to a screw shaft 77 in one direction to extend the actuator and thus raise the insulating block 71 and microtiter plate 11, and in the opposite direction to retract the actuator and thus lower the block and microtiter plate. Alternatively, the actuator can be a power (e.g., pneumatic) actuator with suitable controls.

The light source 31 may be of any suitable type, such as a 12-volt deuterium or tungsten lamp or a 254-nm mercury lamp, emitting light having a certain wavelength (e.g., 200–800 nm and generalizable to other wavelengths) corresponding to the absorption band of the sample components of interest. The light is typically ultraviolet or visible light.

Figure 8:
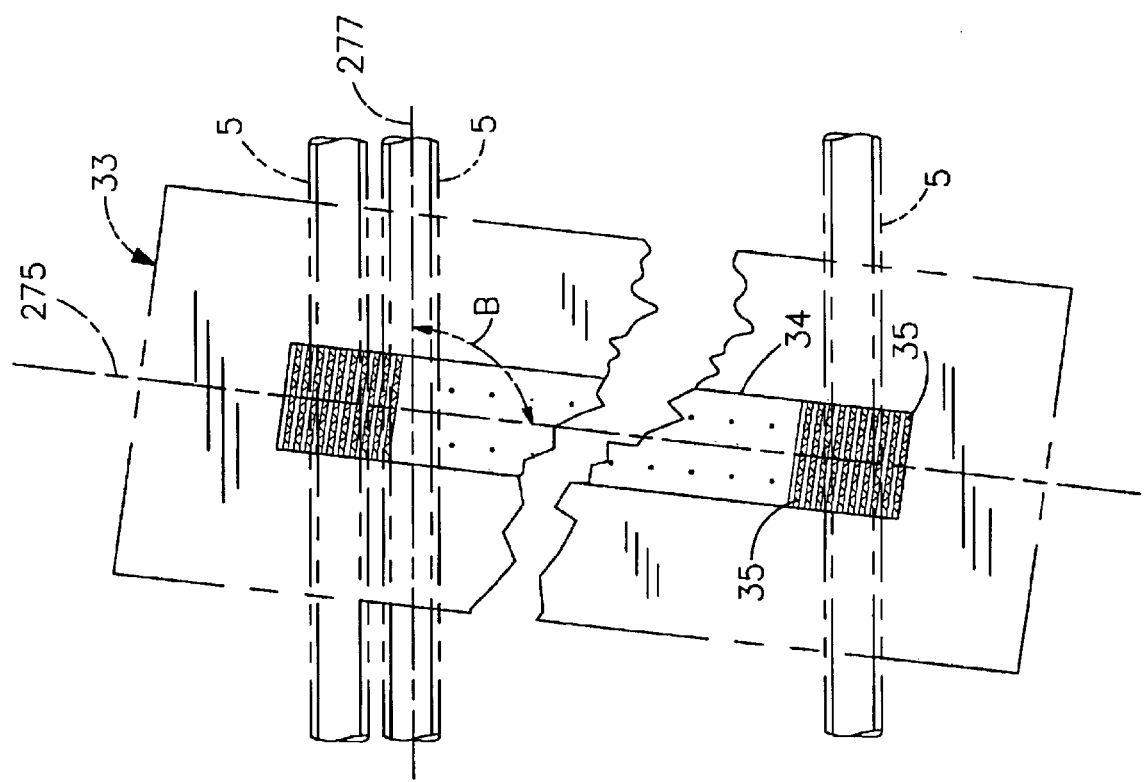
FIG. 8 is a view of a linear array of photodetector elements and an image of capillary tubes projected on the array, the linear array being skewed relative to the lengths of the tubes.
Figure 9:
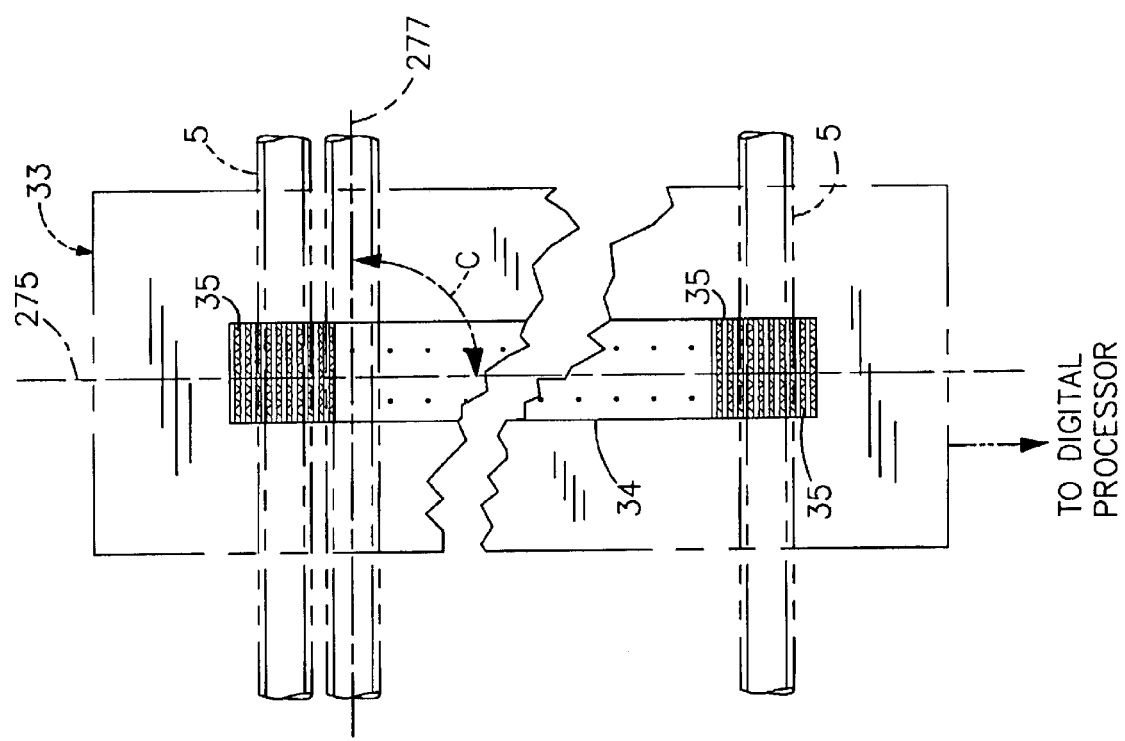
FIG. 9 is a view similar to FIG. 8 but showing the linear array rotated to a position generally perpendicular to the lengths of the tubes.

The photodetector 33 is of a conventional type, such as a photodiode device, having the aforementioned linear array 34 of photodetector elements 35 (FIGS. 8 and 9). These elements may be photodiodes, for example, arranged in one or more linear rows. For example, the photodetector 33 may be a model C5964 multichannel detector head by Hamamatsu incorporating a linear image sensor chip, a low-noise driver/amplifier circuit, and a temperature controller. In this example, the linear image sensor chip has 1024 diodes, each of which is 25 microns in width and 2500 microns height. Other types of photodetectors 33 can be used without departing from the scope of this invention. The photodetector elements 35 generate output signals which are then transmitted to a digital processor 83 (FIG. 1) and related equipment (e.g., a computer 85) for generating and displaying an electropherogram, i.e., a plot of light intensity versus time, as will be understood by those skilled in this field. This plot can then be evaluated to identify components of interest in the samples being analyzed. As shown in FIG. 1, the electropherogram 87 can be displayed on a screen 89 of the computer 85.

The imaging lens 39 may also be of conventional design, such as a quartz lens (Sodern; f.1.=94 mm; F=4.1) in combination with an interference filter 93 (Oriel) employed to define the absorption wavelength. The lens 39 is positioned between the detection window 47 and the photodetector 33 to receive light passing through the capillary tubes 5 and to image that light on the linear array 33 of photodetector elements 35. The image of the capillary tubes 5 projected by the lens 39 on the photodetector 33 may be an image 1.5 times actual size, for example.

Figure 4:
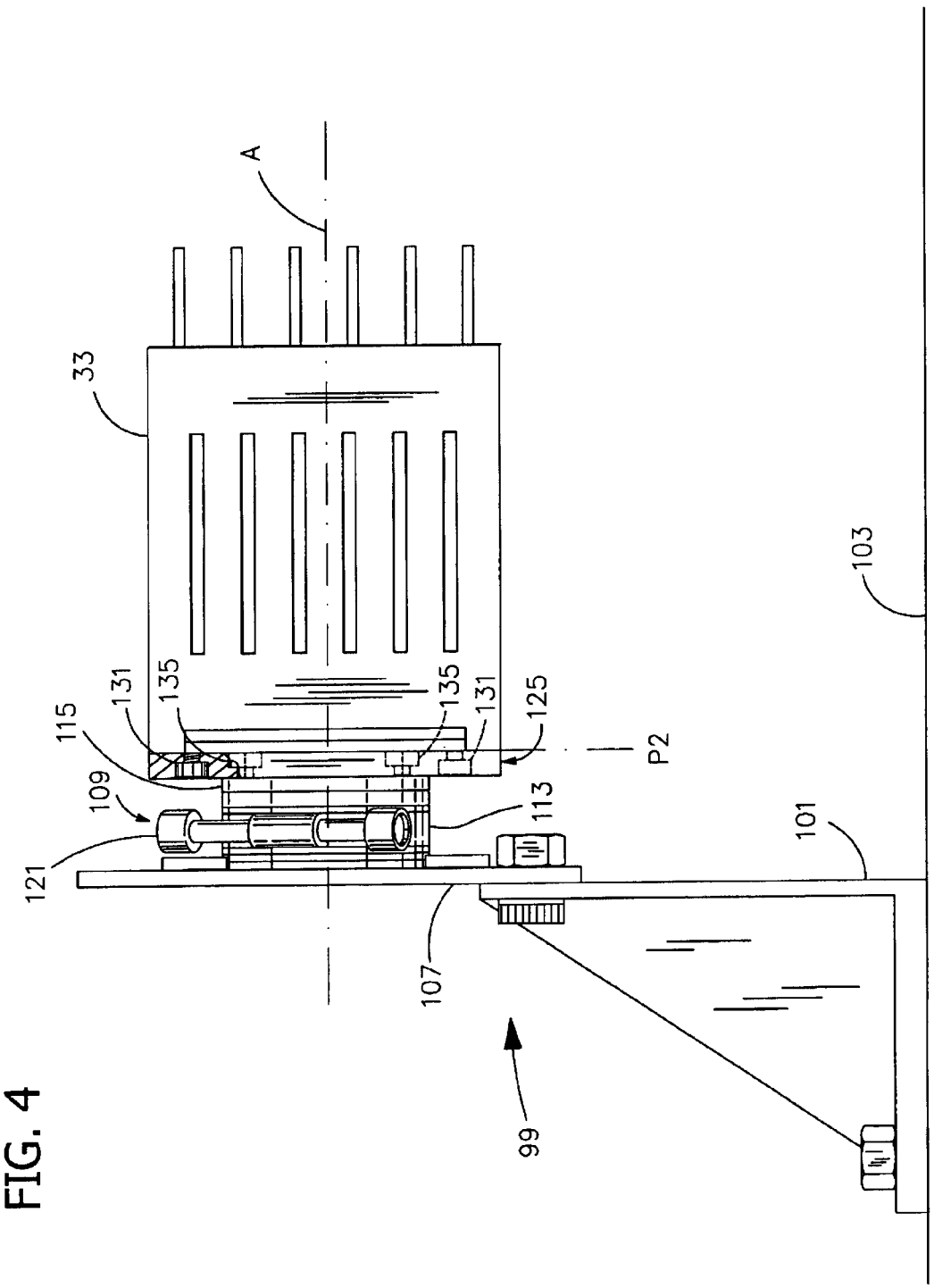
FIG. 4 is a side elevation of a photodetector mounted on a rotational stage.
Figure 5:
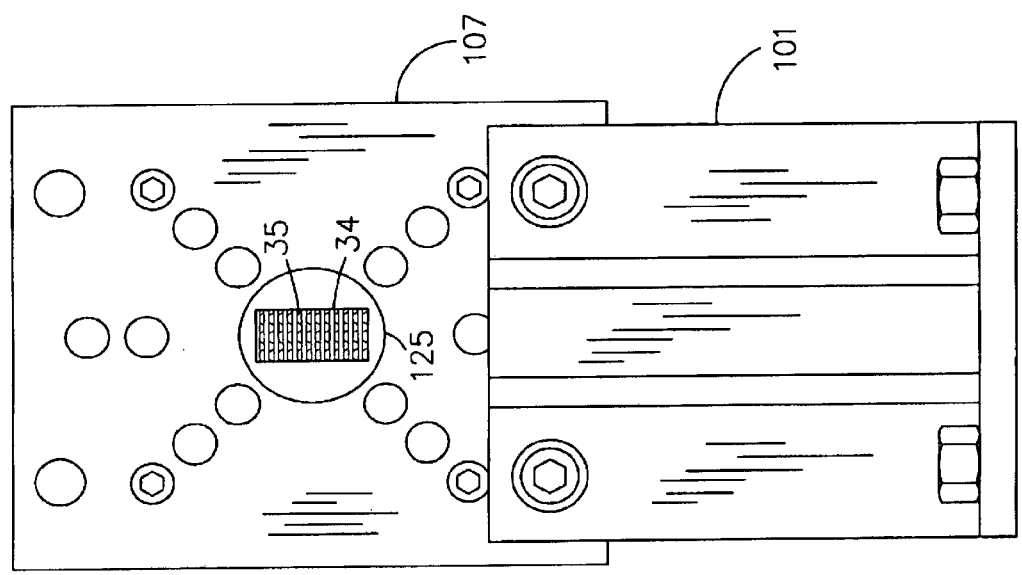
FIG. 5 is a front elevation of a mount for the rotational stage.

Referring to FIGS. 1 and 4, a mounting assembly, generally designated 99, is provided for mounting the photodetector 33 for rotation about a generally horizontal axis A. This assembly 99 comprises a bracket 101 attached to the floor 103 of an enclosure to be described later in detail, a vertical mounting plate 107 attached to the bracket and extending up from the bracket, and a rotational stage, generally designated 109, attached to the mounting plate. The rotational stage 109 comprises a stationary ring unit 113 attached to the mounting plate 107, and a rotatable ring unit 115 concentric with the stationary ring unit and rotatable relative thereto about the aforesaid horizontal axis A. The rotational stage 109 has a gross angular adjustment (e.g., a set screw arrangement not shown) whereby the rotatable ring unit 115 can be quickly rotated to an approximate angular position, and a fine angular adjustment (e.g., a screw-type adjustment 121) whereby the angular position of the rotatable ring unit can be slowly moved to a precise position, the angular adjustment mechanism then functioning to hold or maintain the ring unit in such precise position until such time as further adjustment is required. Alternatively, a locking mechanism separate from the angular adjustment mechanism may be used to maintain the rotatable ring unit in its adjusted position. The vertical mounting plate 107 has a central opening 125 therein aligned with the openings in the ring units 113, 115. The type of rotational stage 109 shown in the drawings is generally of a type which is commercially available, e.g., Model UTR Series Manual Rotary Stage sold by Newport Corporation of Irvine, Calif.

Figure 6:
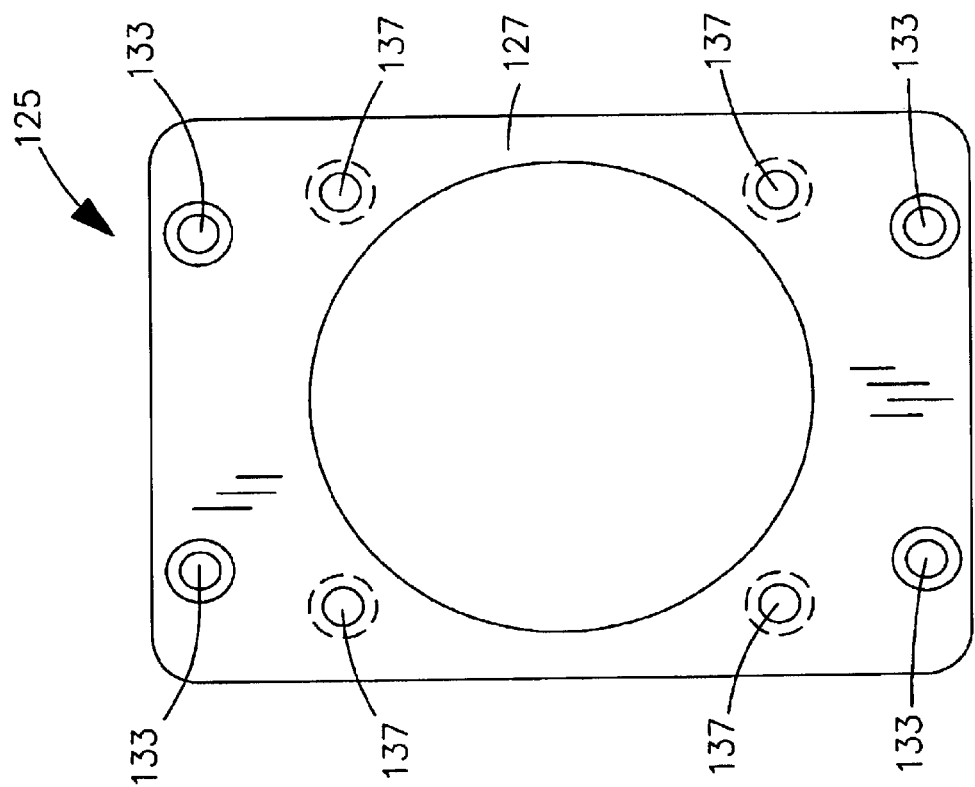
FIG. 6 is a front view of an adaptor plate for mounting the photodetector on the rotational stage.
Figure 7:
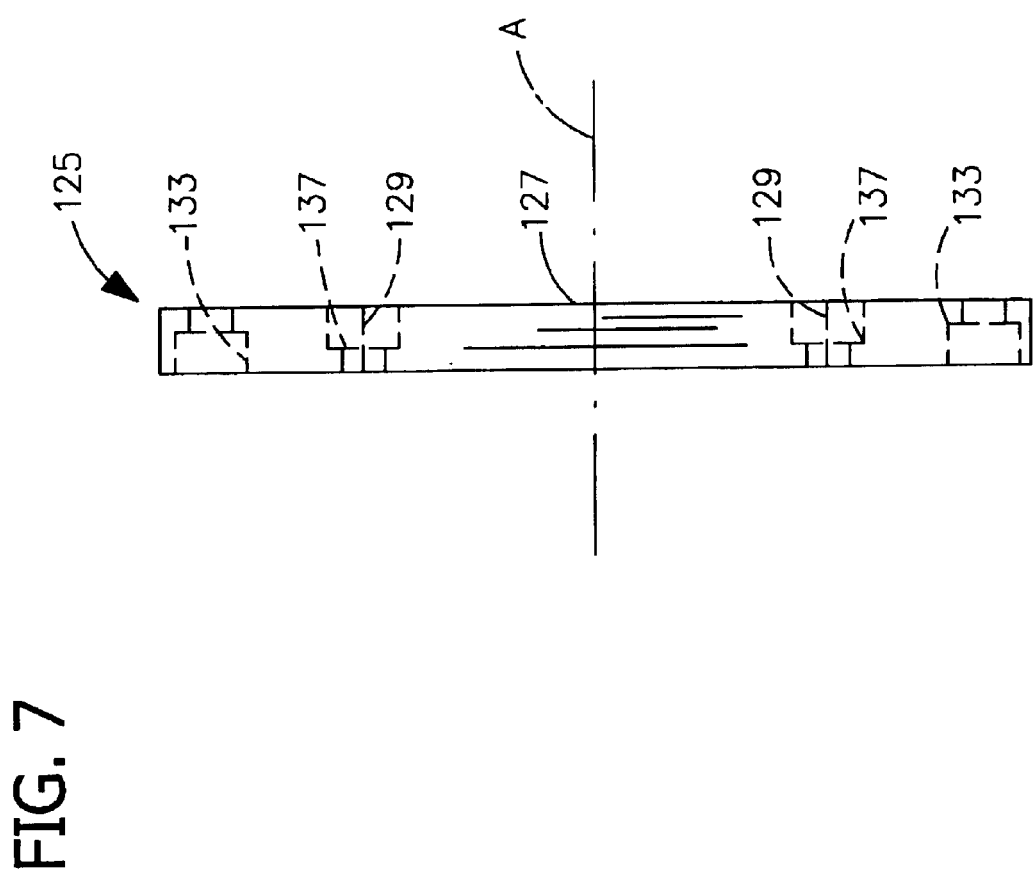
FIG. 7 is a side view of the adaptor plate.

Referring to FIGS. 4, 6 and 7, means generally indicated at 125 is provided for attaching the photodetector 33 to the rotatable ring unit 115 of the rotational stage 109. This means comprises an adaptor, also designated 125, comprising a frame 127 of suitable material (e.g., anodized aluminum) defining an opening 129, fasteners 131 (e.g., screws) receivable in fastener openings 133 in the frame for fastening the adaptor to the front face of the photodetector 33 with the opening 129 in the frame aligned with the linear array 34 of photodetector elements 35, and fasteners 135 (e.g., screws) receivable in fastener openings 137 in the frame for fastening the adaptor to the rear face of the rotatable ring unit 115 of the rotational stage 109 with the frame opening 129 aligned with the opening in the ring unit 115, the openings in the two ring units 113, 115 and the adaptor 125 being sufficiently large to expose the entire linear array 34 of the photodetector 33 to light transmitted by the lens 39. When the photodetector 33 is attached to the rotatable ring unit 115, the unit can be rotated on axis A to adjust the angular orientation of the linear array 34 of photodetector elements 35 relative to the image of the capillary tubes 5 projected by the lens 39 onto the photodetector. Suitable markings (not shown) are provided on the ring units 113, 115 for reading the angular orientation of the rotatable ring unit 115 relative to the stationary ring unit 113. The markings should be sufficiently close together to measure very small increments of rotation (e.g., 1/60 of one degree) to provide very fine adjustment.

Other types of rotational stages and/or mounting assemblies for the photodetector 33 may be used without departing from the scope of this invention. Also, the rotatable ring unit 115 of the rotational stage 109 may be rotatable manually or by a suitable motorized mechanism.

Referring now to FIG. 1, the cooling system 43 of the present invention comprises a thermally insulated enclosure 145 enclosing the bundle 3 of capillary tubes 5, light source 31 and photodetector 33. The cooling system includes a first heat transfer mechanism comprising a conduction heat transfer mechanism, generally designated 151, for cooling the array 23 of closely spaced intermediate portions 21 of the capillary tubes, where the density of the tubes generates a substantial amount of concentrated heat, and a second heat transfer mechanism comprising a pair of convective heat transfer units, each generally indicated at 155, for cooling the inlet end portions 7 of the tubes 5 which, unlike the intermediate portions 21, are spread apart and not closely packed.

The enclosure 145 can be in the shape of a large box, having front doors 161 for access to the interior of the enclosure. The enclosure is provided with a layer of thermal insulation 163.

Figure 14:
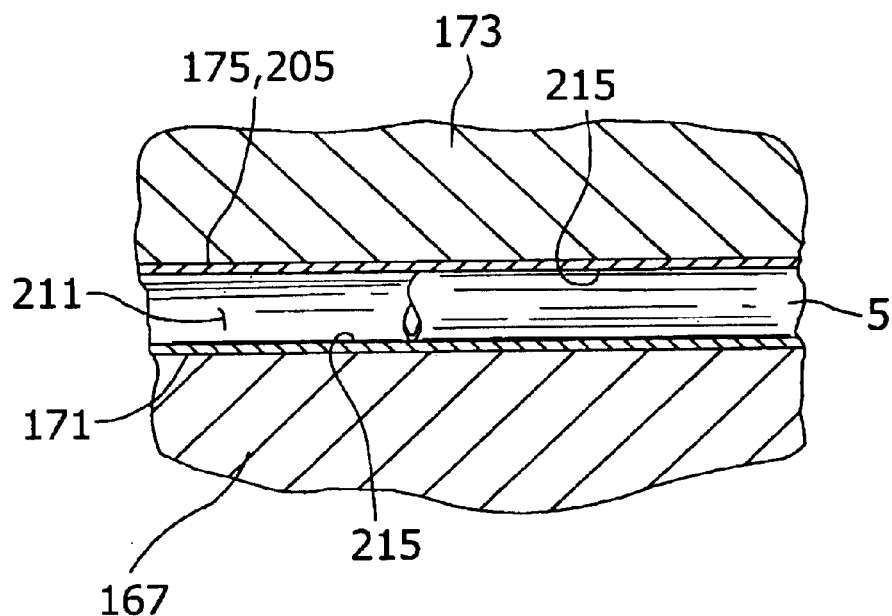
FIG. 14 is an enlarged portion of FIG. 13 showing a capillary tube sandwiched between two slabs of the cooling body, a portion of the tube being removed to show details of construction.
Figure 15:
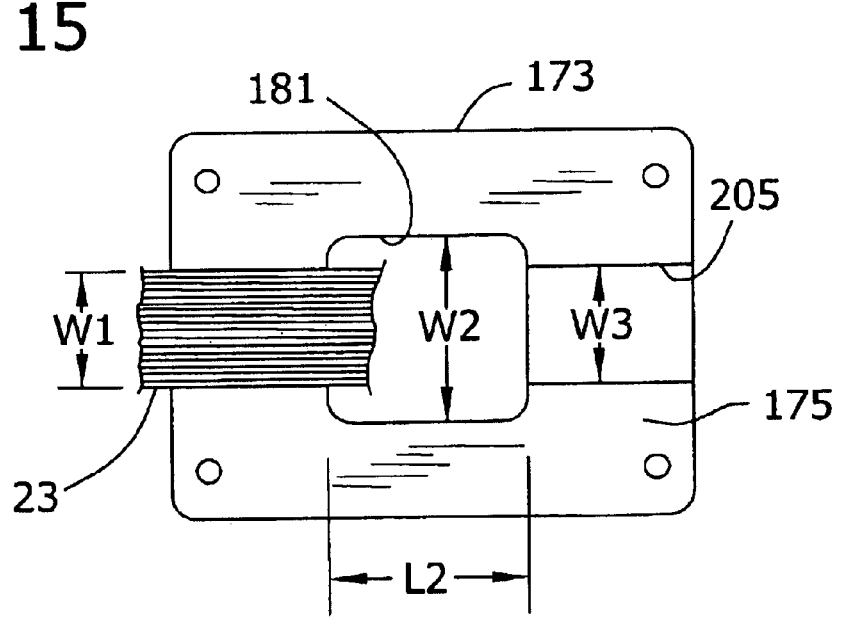
FIG. 15 is a front elevation of a back slab of the cooling body.

In the preferred embodiment shown in FIGS. 2 and 10–15, the conduction heat transfer mechanism 151 comprises a refrigerated body 165 of thermally conductive material (e.g., a metal such as aluminum) having a length L1 and a width W1. The body is supported in the enclosure 145 by a post P and comprises two separate rectangular slabs, i.e., a relatively thick front cooling slab 167 having a front face 169 and a rear face 171, and a thinner back slab 173 having a front face 175 and a rear face 177. The slabs have central aligned window openings 181 therein which combine to form a window, also designated 181, through the body. Referring to FIG. 15, the window 181 has a width W2 greater than the width W of the bundle 3 and a length L2 sufficient to expose the bundle for testing, in this case to permit the passage of light from the light source 31 through the window 181 for incidence on the aforementioned detection window 47 of the capillary bundle 3.

The front slab 167 has passaging therein for the flow of a suitable coolant to cool the slab. (The coolant may be water or other liquid.) This passaging comprises a pair of passages constituted by bores 185, 187 through the slab 167 located on opposite sides of the window 181. The bores 185, 187 are sealingly connected by flexible tubing, as indicated at 191. Bore 187 has an inlet end for connection to a coolant supply line 195 of a suitable refrigeration system 197, and bore 185 has an outlet end for connection to a coolant return line 201 of the same refrigeration system. The refrigeration system 197 may be conventional, such as a Model RTE Series refrigerated bath and recirculating system commercially available from NESLAB Instruments, Inc. of Portsmouth, N.H. This system has a temperature control, including a temperature sensor (not shown) for sensing the temperature of the cooling body 165, so that the temperature of the body can be regulated.

As illustrated best in FIG. 15, the back slab 173 has a channel 205 in its front face 175 which extends the full length L1 of the slab about midway between opposite sides of the slab (the top and bottom sides as shown). When the back slab 173 is attached to the front slab 167, as by fasteners 207, the rear face 171 of the front slab 167 and the walls of the channel 205 combine to define a recess 211 (FIG. 14) which is generally rectangular in horizontal section for receiving the bundle 3 of capillary tubes 5. This recess 211 has a width W3 (FIG. 15) slightly greater than the width W of the bundle 3 at the detection window 47, and a depth (front-to-back direction) which is approximately equal to the diameter of a capillary tube 5 of the bundle, so that the tube is positioned sufficiently close to the rear cooling face 171 of the front slab 167 for the efficient transfer of heat from the tube (and its contents) to the body 165. Preferably, the bundle 3 is in contact with the cooling face 171, but actual contact is not essential so long as sufficient cooling is provided. The recess 211 is positioned relative to the window 181 so that when the bundle 3 is in position, the bundle is aligned with the window so that light transmitted through the window will pass through the capillaries.

The front and back slabs 167, 173 are electrically insulated from the capillary tubes 5 by coatings 215 of a suitable dielectric material (e.g., alumina from an anodizing process) applied at least to the rear face 171 of the front slab 167 and the front face 175 of the back slab 173 (FIG. 14). The coating 215 should be thermally conductive and may have a thickness of 0.5–2.0 $\mu$m, for example.

Figure 11:
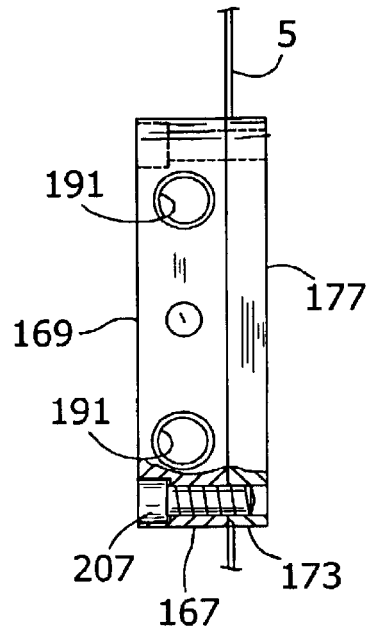
FIG. 11 is a side elevation of the cooling body of FIG. 10.
Figure 12:
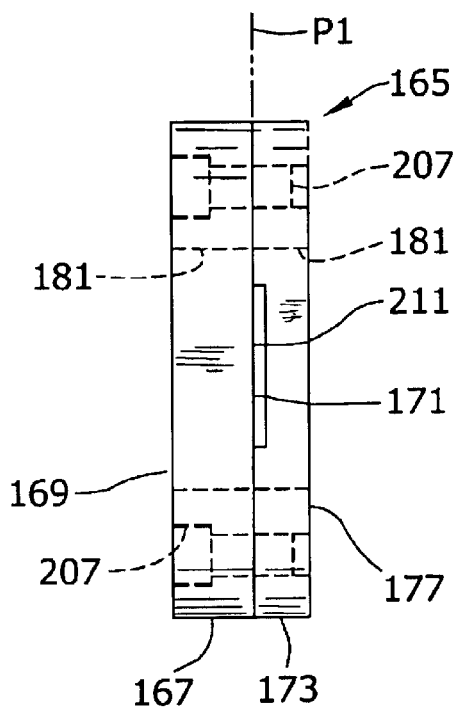
FIG. 12 is a side elevation of the cooling body, with the capillary tubes removed.
Figure 13:
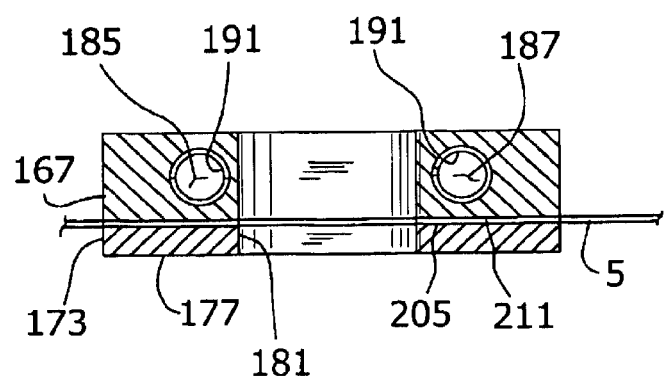
FIG. 13 is vertical section on line 13—13 of FIG. 10.

The fasteners 207 for connecting the two slabs 167, 173, are illustrated in FIG. 11 as bolts received in holes adjacent the four corners of the slabs, the holes in the front slab 167 being non-threaded clearance holes which are counterbored to receive the heads of the bolts, and the holes in the back slab 173 being tapped. Other fastening arrangements may be used.

The slabs 167, 173 may be dimensioned according to the required cooling requirements. Preferably, the slabs have a length L1 sufficient to cover a substantial portion of the length of the bundle 3 to provide the desired cooling. The slabs 167, 173 should also have a sufficient mass and thermal conductivity to be quickly responsive to temperature adjustments which may be made, as by the aforementioned temperature control of refrigeration system 197.

Other heat transfer mechanisms may be used for cooling the closely spaced array of capillary tubes 5. For example, a thermoelectric device can also be used.

Each convective heat transfer unit 155 comprises a heat exchange device 221 having a cooling surface and a fan 225 for circulating air over the cooling surface and directing such air in an appropriate direction. One of the two units 155 is preferably located adjacent the inlet end portions 7 of the capillary tubes 5 for circulating cool air thereover; the other is preferably located adjacent the photodetector 33, as illustrated in FIG. 1. The two heat exchange devices 221 are operable to maintain the air temperature inside the enclosure in the range of 0–90 degrees C., and preferably at about 10 degrees C. Suitable convective heat transfer units of the type described are available, one such unit being available under the trade designation Kodiak Recirculating Chiller—RC022J02BG3 from Lytron Inc. of Woburn, Mass. Other devices may also be used for circulating cooling air inside the enclosure 145 without departing from the scope of this invention.

Figure 16:
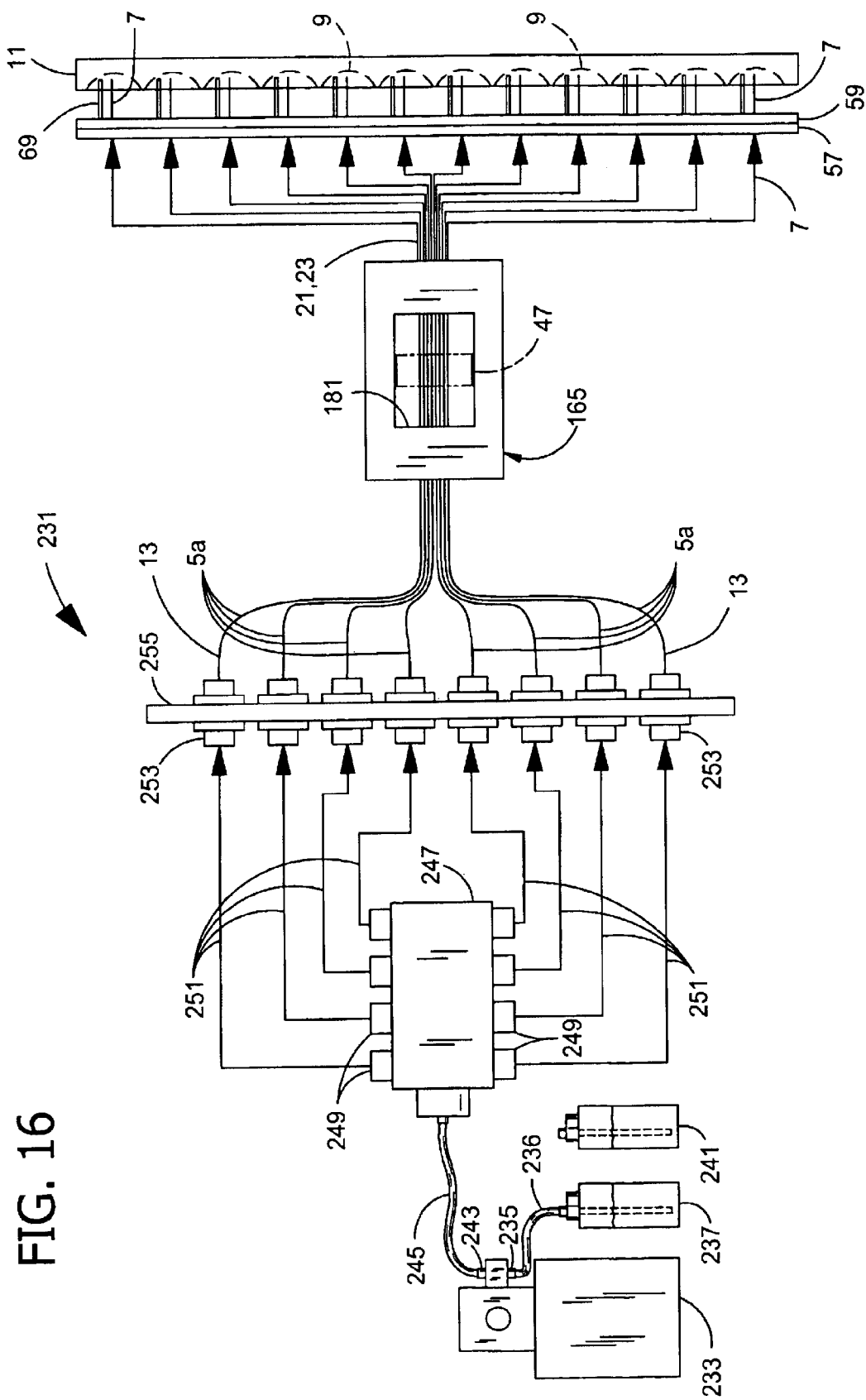
FIG. 16 is a schematic view of a cleaning and buffer loading system.

FIGS. 1 and 16 illustrate a system generally designated 231, for flushing the capillary tubes 5 and also for loading the tubes with a suitable buffer solution prior to conducting an actual sample separation process. The system 231 includes a pump 233 having an inlet 235 for selective connection via a line 236 to a first container 237 containing a supply of flushing solution (e.g., water or an aqueous solution of sodium hydroxide) or to a second container 241 containing a supply of buffer solution (e.g., cyclodextrin for chiral separation). The pump 233 has an outlet 243 connected via line 245 to a manifold 247 having a series of outlet ports 249. Each outlet port 249 is connected to a conduit 251 which extends to one end of a fitting 253 mounted on a support 255 in the enclosure 145, the other end of the fitting being connected to a group 5a of capillary tubes. (For example, a capillary bundle consisting of 96 capillary tubes may be divided into eight groups 5a of 12 tubes each, and each group may be connected to a respective fitting 253.) The arrangement is such that the pump 233 may be operated to pump liquid from the appropriate container 237, 241 for delivery to the capillary tubes 5 via line 245, manifold 247, conduits 251 and fittings 253. The fittings are of conventional design and commercially available, e.g., from Valco Instruments Company, Inc. of Houston, Tex.

In use, the CE system 1 of the present invention is set up as shown in FIG. 1, where the array 23 of the intermediate portions 21 of the parallel capillary tubes 5 lie in a first plane P1 within the channel 205 of the cooling body 165, where the photodetector 33 is mounted on the rotational mount 109 in a position in which the linear array 34 of photodetector elements 35 lies in a second plane P2 generally parallel to the first plane P1, and where the axis of rotation A is generally perpendicular to the two planes P1, P2. (As used herein, "generally parallel" includes an arrangement where the two planes P1, P2 are off parallel by as much as 5 degrees. Similarly, "generally perpendicular" includes an arrangement where the axis A is off perpendicular by as much as 5 degrees.)

The capillary tubes 5 are cleaned ("conditioned") and prepared prior to the start of each sample separation run.

This is accomplished by connecting the outlet end portions 13 of groups 5a of the capillary tubes 5 to respective fittings 253 on the support 255, and then operating the pump 233 to pump cleaning solution from the cleaning solution receptacle 237 through the capillary tubes, the flow being in a direction toward the inlet end portions 7 of the tubes. A microtiter plate 11 is positioned on the insulating block 71 to receive cleaning solution as it exits the tubes. After the capillary tubes 5 have been flushed (e.g., "conditioned"), the inlet 235 of the pump 233 is connected to the container 241 containing buffer solution, and the pump is then operated to fill the capillary tubes with buffer solution. After the capillary tubes are properly cleaned and prepared, samples are loaded into the tubes. Sample loading is accomplished by disconnecting the outlet end portions 13 of the capillary tubes from their respective fittings 253 and placing the outlet end portions in the waste receptacle 15. A microtiter plate 11 containing the samples to be analyzed is positioned on the insulating block 71 with the capillary tubes 5 and electrodes 69 extending down into the wells 9 of the plate. The power source is then operated to apply a voltage differential (e.g., 10 kv) across each capillary tube for a period of time (e.g., 10 seconds) suitable to cause the electro-kinetic movement of a quantity of sample from the wells 9 of the microtiter plate 11 into the inlet end portions 7 of the capillary tubes. After samples have been loaded into the capillary tubes, the microtiter plate 11 is replaced by a container of buffer solution so that the inlet end portions 7 of the capillary tubes extend down into the buffer solution. The buffer solution container may be wrapped or otherwise sealed to reduce evaporation of the buffer.

Following sample loading, and prior to the start of an electrophoresis operation, the cooling system 43 is actuated to cool the interior of the enclosure 145 and the capillary tubes 5 therein. This involves actuating the two convective cooling units 155 and also the conduction cooling device 151 for a time sufficient to bring the interior air temperature of the enclosure 145 down to a temperature sufficient to prevent overheating of the capillary tubes and the contents thereof during chiral separation. A temperature in the range of 0–90° C., and preferably about 10° C. or lower, is believed to be suitable for this purpose.

After the enclosure 145 and capillary tubes 5 are suitably cooled, a voltage is applied to the tubes, causing the various components of the samples to migrate at different speeds to effect separation, as will be understood by those skilled in this field. To separate chiral molecules, usually a relatively large current is required (e.g., a sum total of 20 milliamps for a bundle of 96 capillary tubes), which results in the generation of a substantial amount of heat in the tubes and contents thereof. The conduction heat transfer device 151 removes this heat in the area of the bundle 3 generally adjacent the detection window 47, where the capillary tubes 5 are relatively closely spaced. The convective heat transfer units 155 removes this heat from other portions of the bundle, including the inlet end portions 7 of the tubes 5. As a result, overheating of the capillary tubes and contents thereof is prevented, thus ensuring a more accurate analysis of the samples.

Light from the light source 31 passes through the planar array 23 of the capillary tubes and is projected by the lens 39 as an image of the tubes onto the photodiodes 35 of the photodetector 33. These diodes 35 generate signals which are processed in conventional fashion to generate and display an electropherogram 87 plotting light intensity (indicative of absorption levels) versus time. The clarity, resolution and detection limits of this plot can be improved by rotatably adjusting the rotatable ring unit 115 (carrying the photodetector 33) to find the optimal angular position for providing an electropherogram having better clarity, resolution and/or detection limits. The adjustment procedure is best illustrated in FIGS. 8 and 9.

In FIG. 8, it will be observed that the image of the tubes 5 projected on the linear array 34 of photodiodes is at an angle where the longitudinal centerline 275 of the array is skewed at an angle B relative to the centerline 277 of a tube 5. This orientation does not yield an optimal electropherogram, since the photodiode elements 35 are slanted relative to the lengths of the tubes. The characteristics (clarity, resolution and/or detection limits) of the electropherogram can be improved by rotating the rotatable ring unit 115 of the rotational stage 109, and the photodetector 33 mounted thereon, to the position shown in FIG. 9 where the photodiode elements 35 are more aligned with the projected image of the tubes 5. The optimal angle, indicated at C in FIG. 9, is usually about 90 degrees, that is, an angle where the longitudinal centerline 275 of the linear array 34 of photodetector elements 35 is precisely perpendicular to the capillary tubes (i.e., the projected image of the tubes) and the longitudinal centerlines of the elements 35 are parallel to the longitudinal centerlines 277 of the capillary tubes. The optimal angle is identified by rotating the rotatable ring unit 115 one way or the other until the display of the electropherogram 87, as it appears on the screen 89, is optimal in terms of clarity, resolution and/or detection limits. The ring unit 115 is then maintained in this position throughout the separation process. The precise position of the rotatable ring unit 115 relative to the stationary ring 113 unit can be recorded by using the markings on the two units.

It will be understood from the foregoing that the system described above optimizes the results of a parallel CE operation by improving the clarity, resolution and/or detection limits of electropherograms generated during the separation and analysis process. This is achieved by a method involving rotating the photodetector 33 relative to the projected image of the capillary tubes to a position in which the array 34 of photodetector elements 35 is at an optimal orientation (e.g., as shown in FIG. 9), relative to the image, and then maintaining the photodetector in such position. The optimal orientation is easily determined simply by watching the electropherogram while rotating the photodetector 33 until the display of the electropherogram is optimal.

It will also be observed that the cooling system 43 of this invention will provide efficient well-regulated cooling of the bundle 3 by using the convective and conductive heat transfer devices 151, 155, the conductive device providing additional cooling of the tubes 5 where they are more closely spaced in the area adjacent the window 181 in the body 165 where the samples in the tubes 5 are exposed for CE analysis. Consequently, even during chiral separation and other CE processes generating large amounts of heat, the temperature of the samples will remain well below boiling to avoid the formation of bubbles in the samples which can cause dielectric breakdown, sparking and other undesirable results adversely affecting sample analysis. The system of the present invention can be used for any parallel or multiplexed CE process, including but not limited to the separation of chiral molecules. It is believed that the system described above is the first parallel CE system designed to effect chiral separation.

Chiral separation using parallel CE can be effected with or without the use of circular dichroism ("CD") which is the differential light absorption properties of left and right circularly polarized light and which is a characteristic spectroscopic property of chiral molecules. When CD is used, the throughput can be greatly improved because the separation of enantiomers is not required resulting in a shorter separation/detection times. CD can be used to quantitatively identify enantiomeric excess in the presence of both enantiomers of a chiral species. The system described above can be modified to use CD by placing a photoelastic modulator between the light source 31 and the detection window 47 of the capillary tubes. The modulator modulates the light between the left and right circularly polarized components. The magnitude of the CD signal is determined by taking the difference between the left and right hand signals at the photodetector 33. CD is commonly determined for absorption but can also be determined from a fluorescence signal in a fluorescence detection (rather than light absorption) system. In such a system, an analyte which emits upon illumination (either naturally or via a chemical tag) can be used. In this case, an intense source, lamp or laser, illuminates the capillary array and the resulting emission is detected by the diode array.

While the cooling system of the present system is an important aspect of the present invention, it is contemplated that cooling of the bundle 3 during parallel CE may not be necessary under all circumstances, in which case the cooling devices 151, 155 and/or enclosure 145 may be eliminated.

Figure 17:
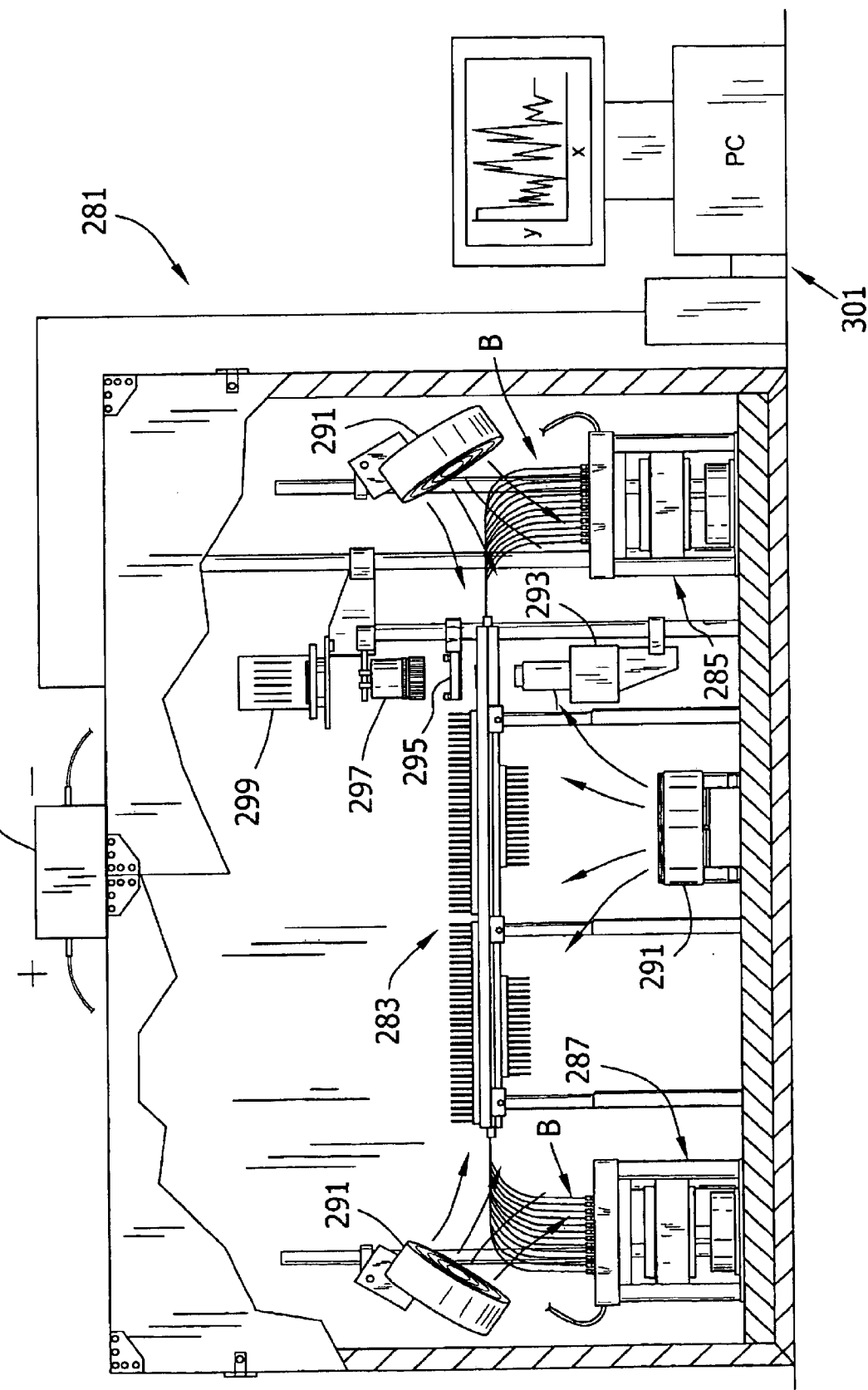
FIG. 17 is a schematic view of an alternative CE system using a different cooling apparatus of the present invention.
Figure 18:
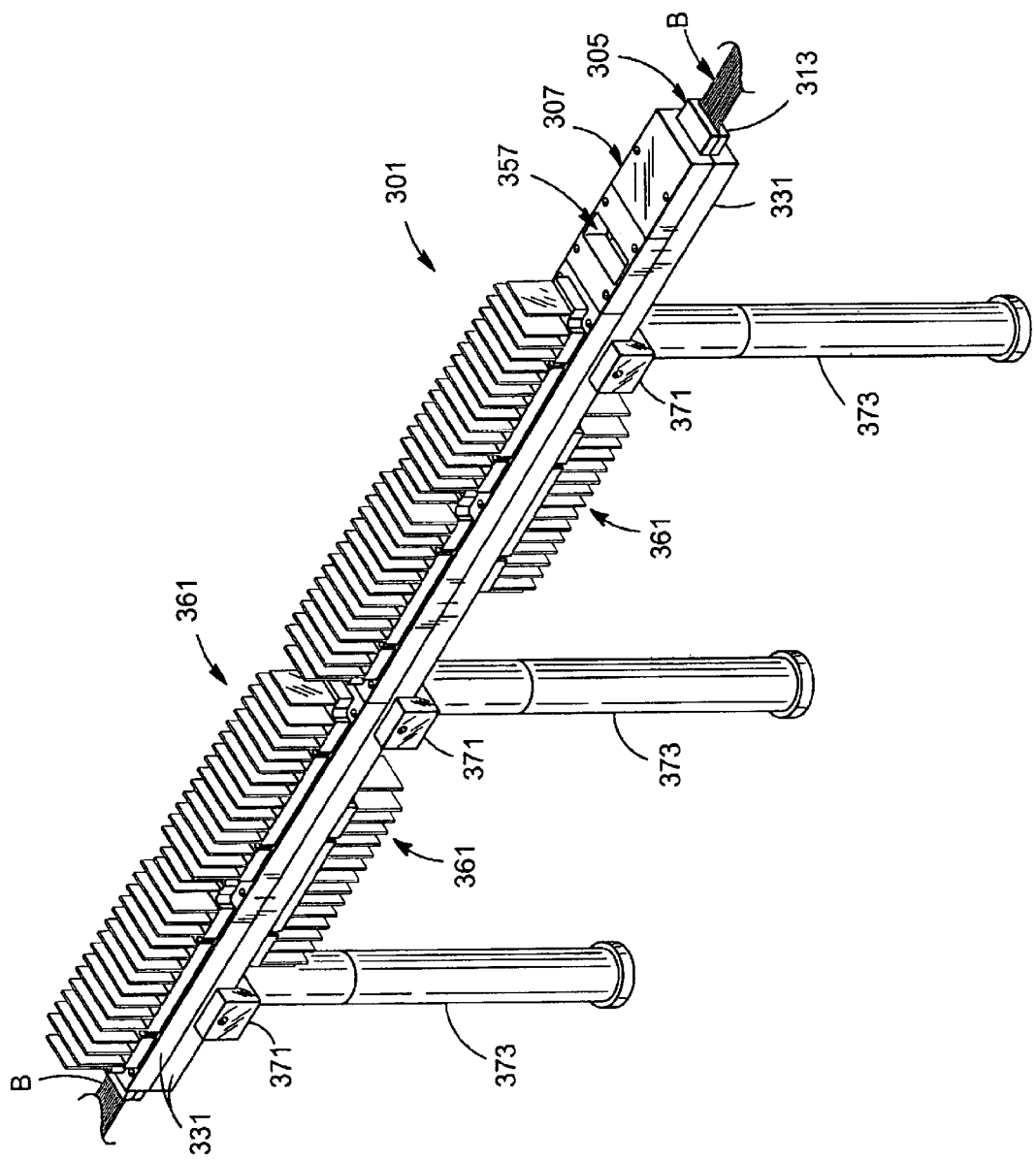
FIG. 18 is a perspective of the cooling apparatus of FIG. 17.

FIG. 17 shows another embodiment of a parallel CE system, generally designated 281. The system includes different cooling apparatus comprising a solid-state cooling device, generally designated 283, for cooling a bundle B of capillary tubes. The system also includes a pair of hydrodynamic injectors 285, 287 at opposite ends of the bundle for conditioning and filling the tubes of the bundle. One of the injectors (285) is grounded and the other (287) is connected to a suitable power source 289 similar to the power source 27 of system 1. The construction and operation of these injectors 285, 287 are described in detail in pending application Ser. No. 9/620,987, filed Jul. 21, 2000, by Peijun Cong et al., entitled Hydrodynamic Injector, assigned to Symyx Technologies, Inc., and incorporated by reference herein. The injectors eliminate the need for the pump 233, manifold 247, fittings 253 and support 255, among other things, of the system 1 of the first embodiment. As a result, there is no need to make the many fitting connections and disconnections during conditioning and filling, thereby reducing the risk of damage to the capillaries. A number of fans 291 are provided for blowing cooling air on the injectors 285, 287 and the cooling device 283 to be described. Like system 1 describe above, the system 281 of this embodiment includes a light source 293 (e.g., deuterium lamp) for emitting light to pass through the capillary tubes in a manner to be described, a bandpass filter 295, a lens 297 and a photodiode array detector 299 connected to a suitable digital processor and related equipment 301.

FIGS. 18–24 show details regarding the construction of cooling device 283. This device is designed to contact a bundle B of capillary tubes over a major portion of its overall length, and preferably over as much of the bundle length as possible, to provide adequate cooling during a CE procedure generating substantial heat. In most cases the cooling device will extend over at least 50% of the overall length of the bundle, and preferably over at least two-thirds of the overall bundle length.

In the particular embodiment shown in FIGS. 18–24, the solid-state cooling device comprises inner and outer jackets designated 305 and 307, respectively. The device also includes a cushion, generally indicated at 309 in FIG. 24, inside the inner jacket for protecting against damage to the capillary tubes placed inside the jackets. These components are described in more detail below.

The inner jacket 305 of the particular embodiment shown in the drawings comprises opposing elongate inner jacket members in the form of channel-shaped slabs 313. The slabs have opposing webs 315 and flanges 317 which combine to define recesses for receiving the aforementioned cushion therein 309. (The precise shape of the inner jacket members 313 is not critical, and configurations other than those depicted in the drawings are contemplated.) The inner jacket members 313 are movable between an open position (FIGS. 18, 23) in which the members are separated to allow placement of the bundle in the jacket, and a closed position (FIG. 22) in which the jacket members are mated together in a position in which they surround the capillary tubes of the section of the bundle B placed in the jacket. The inner jacket 313 members are of a solid, thermally conductive, electrically insulating material. This material is preferably a ceramic-like material having excellent thermal conductivity and dielectric strength characteristics. One such material is boron nitride, which is particularly desirable because it is capable of being machined and is also relatively inexpensive, but other materials (e.g., silicon nitride) may also be suitable. The material used preferably has a thermal conductivity in the range of about 5–50 W/m-K, and more preferably in the range of about 15–50 W/m-K, and dielectric strength in the range of about 20–400 kV/mm, and more preferably in the range of about 40–200 kV/mm. These properties are important to insure proper cooling when high levels of power are applied to the bundle during certain CE procedures. By way of example, when CE is run in the micellar electrokinetic chromatography (MEKC) mode, the amount of power applied to the bundle may range from 150–200 watts, with voltages ranging from 10,000–30,000 volts. The use of this amount of power results in the generation of substantial temperature rises inside the capillary tubes due to Joule heating, and good thermal conductivity is essential to provide adequate heat transfer away from the tubes for adequate cooling. Without such heat transfer, capillary temperatures could rise to levels where the procedure is adversely affected, or where there is a complete failure of the system. Further, high voltages can create static electrical charges on the outside surfaces of the capillary tubes. Accordingly, good electrical insulation properties are necessary to prevent an electrical connection between the ends of the tube through the cooling apparatus. Also, high dielectric strength is necessary to prevent shorting between the capillary and the outer jacket 307, the latter of which typically is of metal, as will be described later.

The cushion 309 is of a thermally conductive, cushioning material. In one preferred embodiment, the cushion comprises a pair of opposing sheets 321 disposed between the inner jacket members 313 on opposite sides of the bundle B and extending the full length of the inner jacket 313. The cushion sheets 321 are preferably of a conformable material, and more preferably an elastomeric material (e.g., a silicone-based elastomer, such as is available from Thermagon, Inc. of Cleveland, Ohio (www.thermagon.com) under the trade designation T-pli 230), although other materials having the requisite thermal conductivity and cushioning characteristics may also be used. In this regard, the thermal conductivity of the cushion sheet material is preferably in the range of about 3–9 W/m-K, and more preferably in the range of about 5–7 W/m-K. The sheet material may also be electrically insulating, although this is not critical. In the embodiment shown in the drawings, the sheets 321 nest within the recesses defined by the webs 315 and flanges 317 of the slabs forming the inner jacket members 313. The cushion sheets 321 are preferably in good thermal contact with at least the webs of the inner jacket members. A suitable thermal grease (e.g., a silicon based zinc oxide grease) can be used between the sheets 321 and inner jacket members 313 to enhance thermal conductivity, if desired. Suitable thermal grease is available from Materials Electronic Products Corporation of Trenton, N.J. (www.melcor.com), under the trade designation TG-001, having a thermal conductivity of about 0.735 W/m-K.

The outer jacket 307 surrounds the inner jacket 305 and may comprise, in one embodiment, mating elongate outer jacket members 331. The outer jacket members 331 are of a thermally conductive material, preferably metal (e.g., aluminum). Each outer jacket member 331 is of generally channel shape, having a base 333 and a pair of spaced side walls 335 extending out from the base. Other configurations are possible. The outer jacket members 331 are movable between an open position (FIGS. 19, 24) in which the parts are separated, and a closed position (FIGS. 18, 21, 23) in which the jacket members are mated together in a position surrounding the inner jacket 305. When the outer jacket 307 is closed, the inner jacket members 313 are received in the recesses formed by the channel shaped outer jacket members, with the webs 315 of the inner jacket members 313 being disposed in thermal conductive relation with the bases 333 of the outer jacket members 331 and with the ends of the flanges 317 of each inner jacket member being generally flush (coplanar) with the free ends of the side walls 335 of a respective outer jacket member 331. A layer of the aforementioned thermal grease may be applied between at least the webs 315 of the inner jacket members 313 and the bases 333 of the outer jacket members 331 to enhance thermal conductivity, if desired. The overall width of each inner jacket member 313 is slightly less than the distance between the side walls 335 of the corresponding outer jacket member 331, so that the fit of the inner jacket member between the side walls of the outer jacket member is relatively close. (Actual contact of the inner jacket members 313 with the side walls 335 of the outer jacket members 331 is not necessary, because the primary path of heat transfer is though the webs and bases of the jacket members.) The distance between the flanges 317 of each inner jacket member 313 will vary depending on the number of capillary tubes in the bundle B, which typically includes 24, 48 or 96 tubes but which may include any number of tubes. In any event, the distance between the flanges 317 should be somewhat greater than the combined diameters of the tubes of the bundle to provide sufficient space to arrange the tubes in an even, side-by-side planar array without undesirable bunching of the tubes which could detrimentally affect the results of the CE procedure.

The inner and outer jackets 305, 307 are secured together by suitable means, such as threaded fasteners (not shown) passing through bores 341 in the side walls 335 of the outer jacket members 331. In one embodiment, tightening of these fasteners functions to draw the inner and outer jacket members 305, 307 closer together, causing the cushion sheets 321 to press against opposite sides of the array of capillary tubes in the apparatus. A small compressive force is desirable (although not essential) for increasing thermal conductivity between the capillary tubes and the cushion sheets 321. The resultant pressure may also assist in enhancing the thermal conductivity between the cushion sheets 321 and the inner jacket members 313, and between the inner jacket members 313 and the outer jacket members 331.

Figure 21:
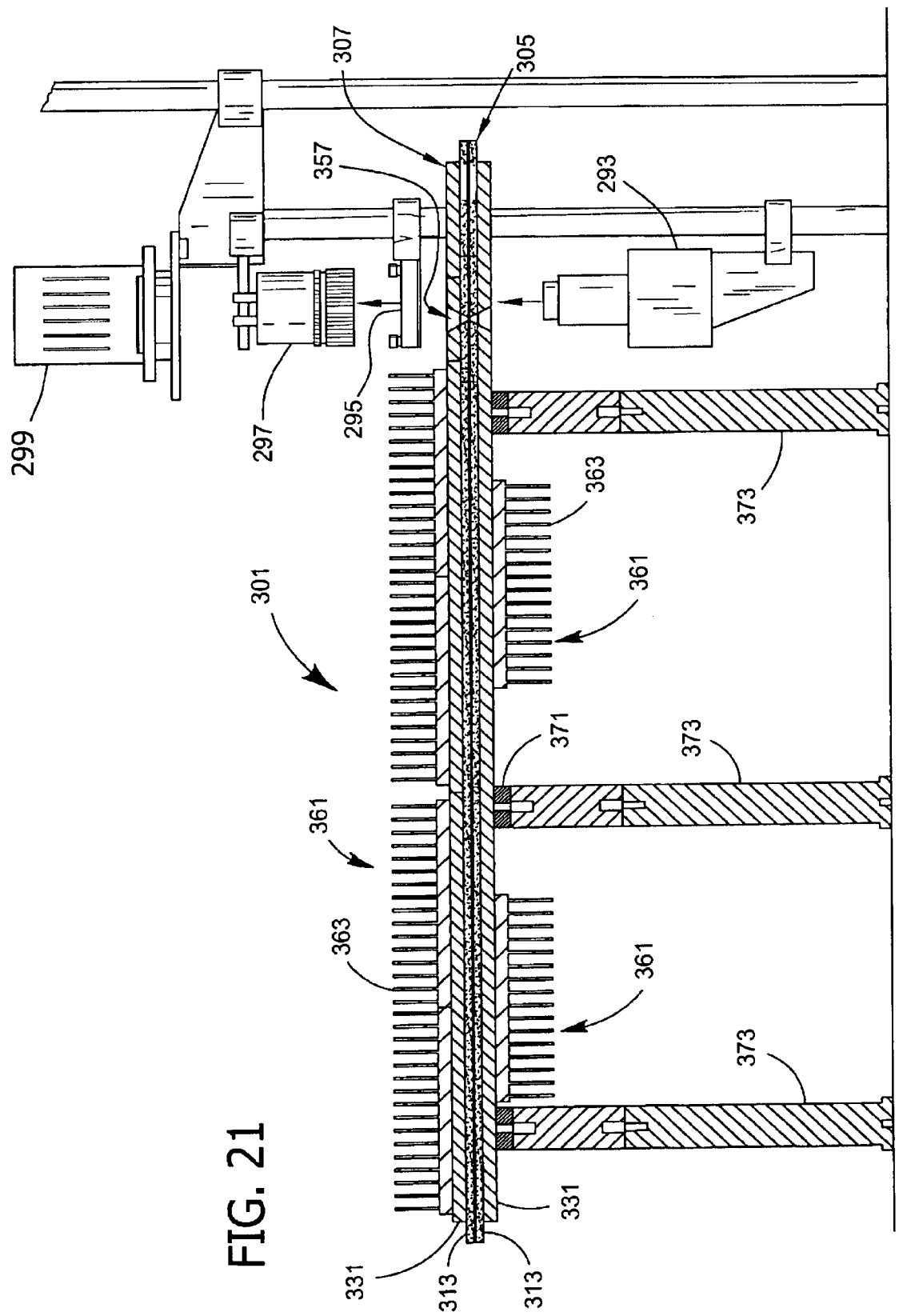
FIG. 21 is a section on line 21—21 of FIG. 20.
Figure 22:
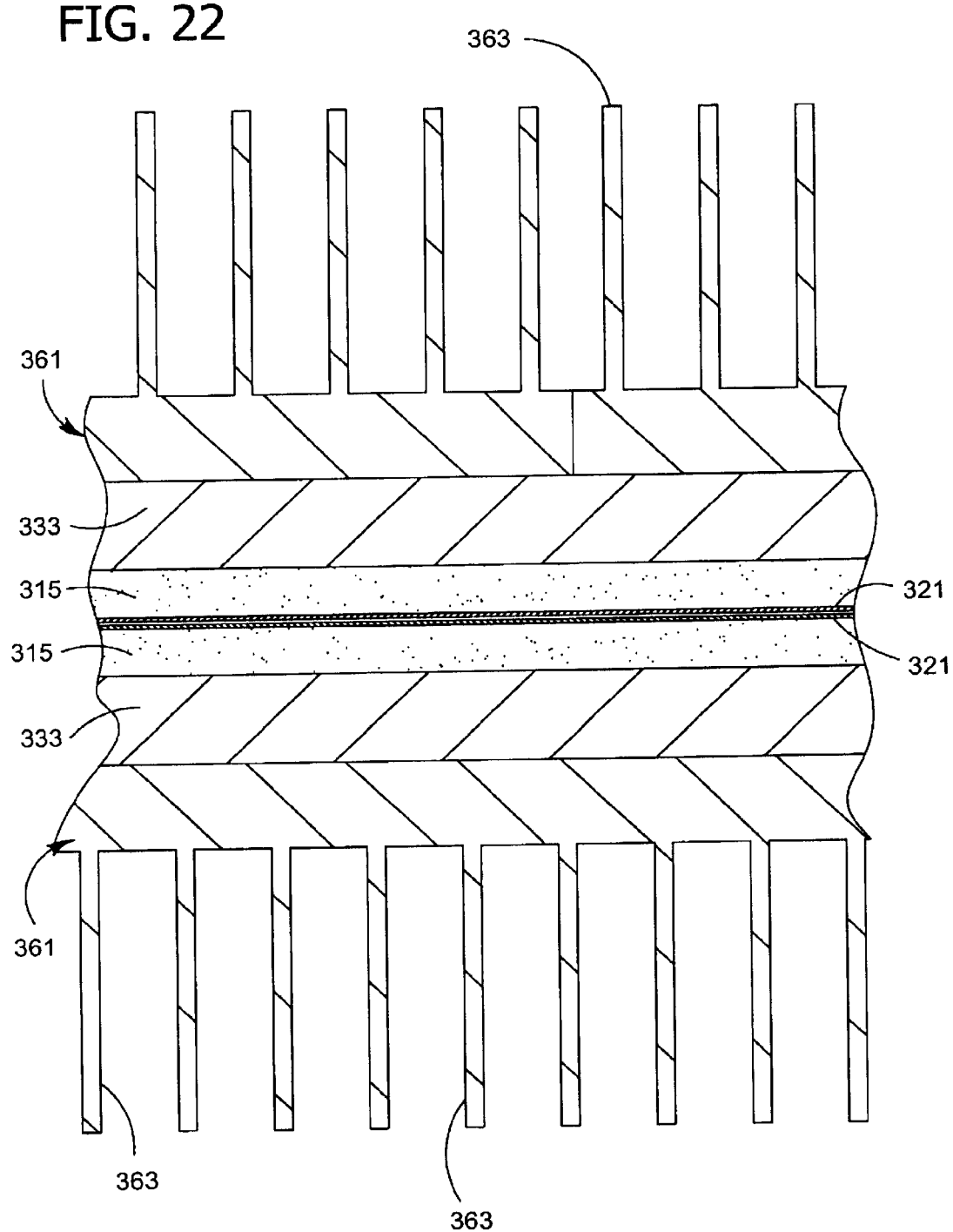
FIG. 22 is an enlarged portion of FIG. 21 showing details of the apparatus and further showing a light source and photo-detector.
Figure 23:
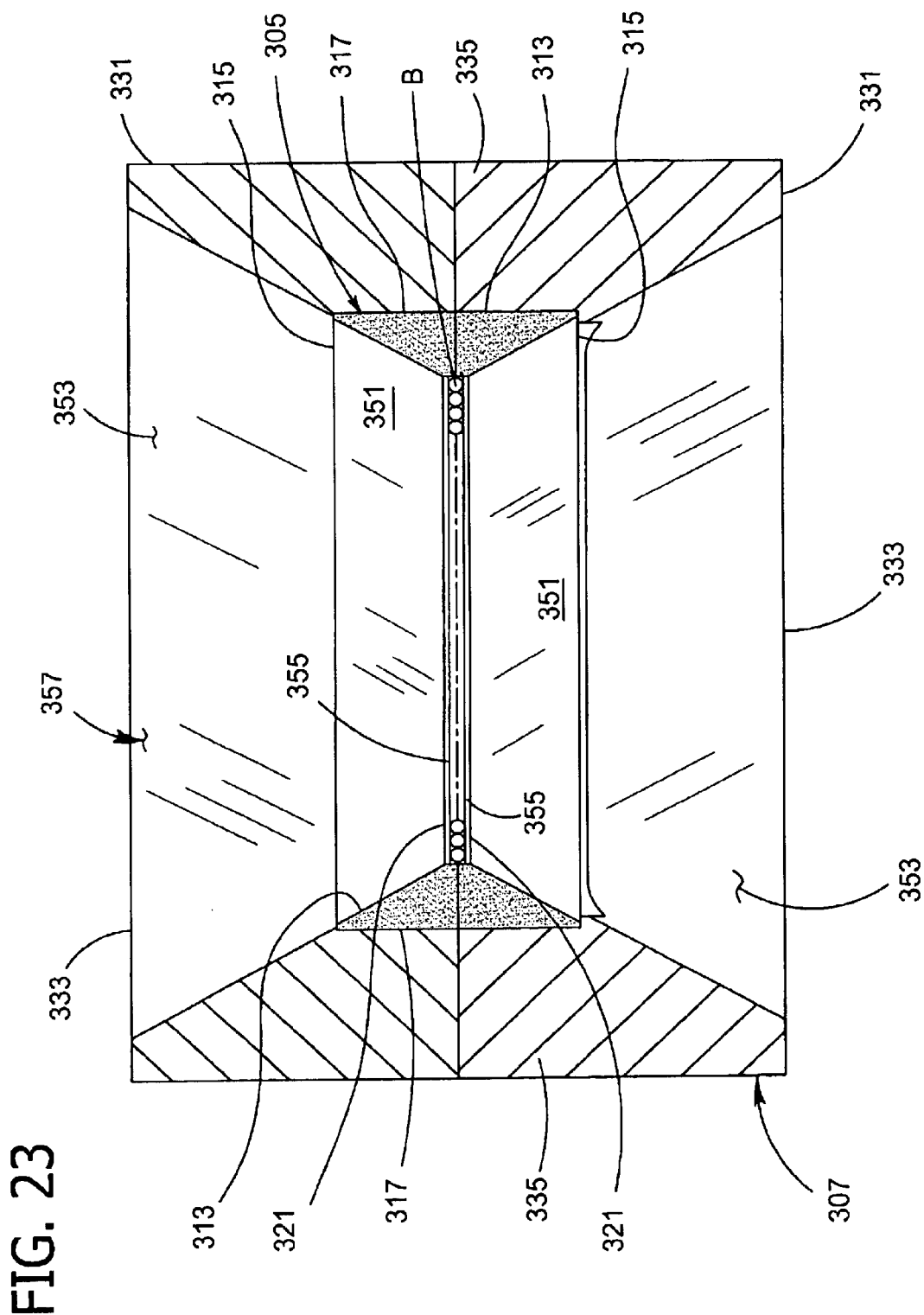
FIG. 23 is an enlarged section on line 23—23 of FIG. 20.
Figure 24:
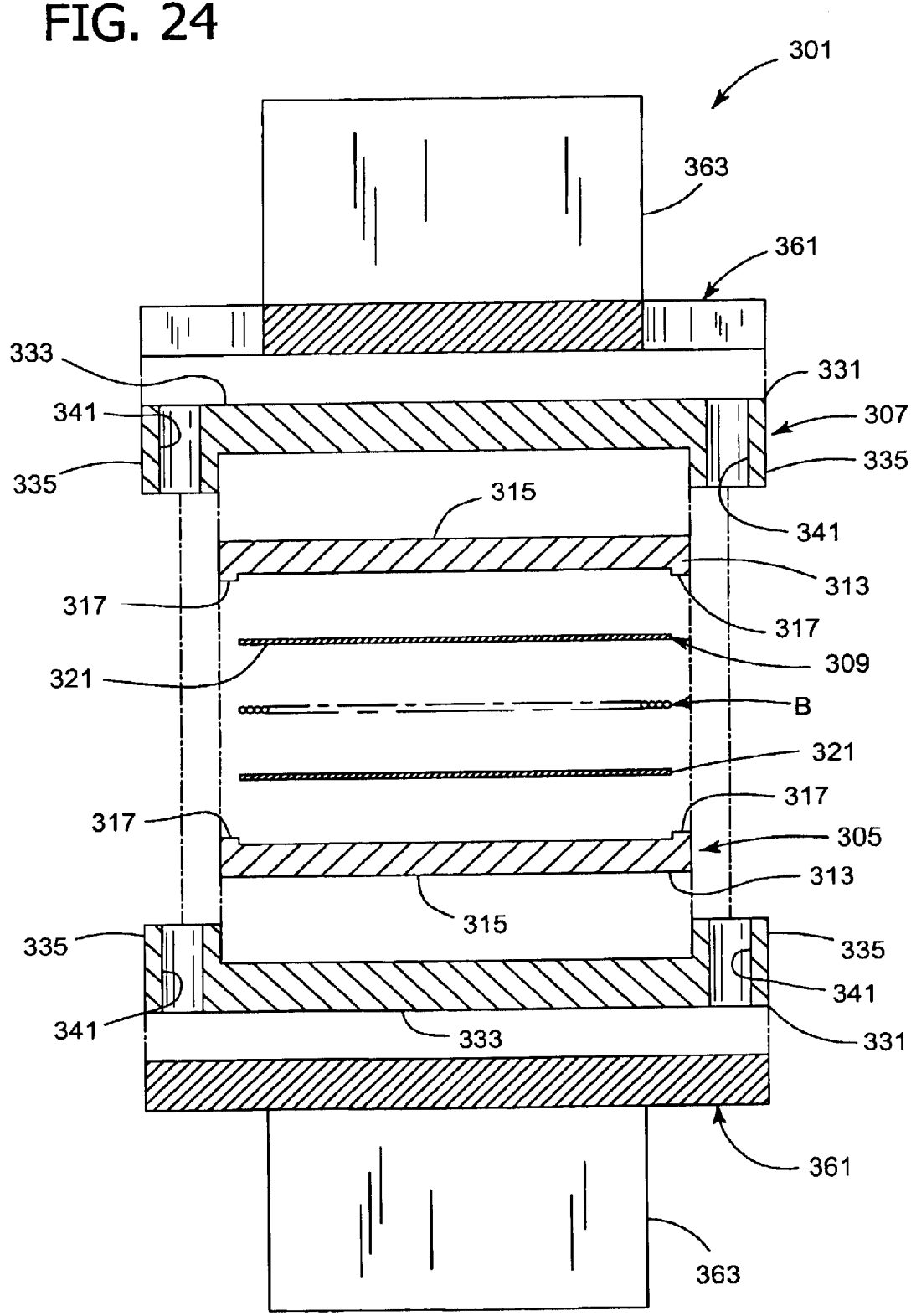
FIG. 24 is an enlarged section on line 24—24 of FIG. but showing the various component parts exploded apart.

The inner and outer jacket members 313, 331 are formed with window openings 351, 353, respectively (FIG. 22). Similarly, the cushion sheets are formed with window openings 355. When the jackets 305, 307 are closed, these window openings 351, 353, 355 align with one another to define a window, generally designated 357, for permitting the passage of light through the window and the capillary tubes of the bundle B at the location of the window. As shown in FIG. 21, the window 357 exposes a portion of a bundle B of capillary tubes contained within the apparatus to light emanating from the light source 293, which may be similar to the light source 31 described earlier in this specification. Light incident on the bundle B creates an image of the bundle which may be projected on the photo-detector 299 (FIG. 21) or other piece of equipment used to analyze the contents of chemical samples passing through the tubes. If a photo-detector is used, it may be similar to the device 33 described previously in this specification. The dimensions of the window 357 are not critical, except to say that the window is preferably relatively narrow lengthwise of the bundle (e.g., 2 mm.)

The outer jacket members may be equipped with one or more heat sinks, each generally designated 361, for increasing the heat absorption and dissipating capacity of the apparatus. In the particular embodiment shown in the drawings, the heat sinks may comprise one or more banks of parallel cooling fins or plates 363 mounted (e.g., fastened) on the base of each of the upper and lower outer jacket members 331. The heat sink 361 may be of any suitable conventional construction, such as a bonded fin heat sink commercially available from, e.g., Materials Materials Electronic Products corporation of Trenton, N.J. (www.melcor.com),part number HX8-202. Fan forced convection may be used to provide additional cooling, if needed.

As illustrated, the inner and outer jackets 305, 307 are elongate and of approximately the same length. This length is preferably sufficient for enclosing a major portion of the length of the bundle B. For example, the jackets may be dimensioned to enclose at least about 50% of the overall length of the bundle, and more preferably about two-thirds of the overall length. (The length of a typical bundle will range from about 20–60 in.) For ease of assembly, and because the inner jacket members 313 may be of a material (e.g., boron nitride) which is available only in certain standard lengths, it may be desirable or even necessary to manufacture the inner and outer jacket members 313, 331 in multiple pieces. In the embodiment shown in the drawings, each inner jacket member 313 is formed in four pieces, as is the upper outer jacket member 331. The lower outer jacket member 331 is formed as a single piece. As will be described later, the jacket pieces are assembled end-to-end to make jacket members 313, 331 of the appropriate length.

The cooling apparatus 383 may be mounted in the generally horizontal position shown in FIG. 17 with one outer jacket member 331 disposed above the other outer jacket member 331. In this embodiment, the lower outer jacket member 331 is held by a plurality of brackets 371 supported by posts 373. The posts are preferably of an electrically insulating material (e.g., Delrin®) to electrically isolate the outer jacket 307 from its surroundings. It will be understood that the cooling apparatus could be mounted in other orientations and using other types of supports.

To use the cooling apparatus shown in FIGS. 17–24, the inner and outer jackets 305, 307 are disassembled to expose the lower outer jacket member 331 so that a thin layer of thermal grease may be applied to the upper surface of the base 331 of the jacket member. The lower inner jacket member 313 is then placed between the side walls 335 of the outer jacket member 331 and slidably moved (rubbed) back and forth along the base 333 until good thermal contact between the web 315 of the inner jacket member and the base 333 of the outer jacket member is established and the window openings 351, 353 in the two lower jacket members 313, 331 are in alignment. The lower cushion sheet 321 is placed over the web 315 of the inner jacket member 313 and a window opening 355 is cut in the cushion sheet in alignment with the window openings in the jacket members therebelow. The window opening 355 could also be pre-cut in the cushion sheet 321. Alternatively, the cushion sheet could be divided into two longitudinal sections spaced apart to define a window opening. In any event, a layer of thermal grease can be applied, if desired, between the lower cushion sheet 321 and the web 315 of the lower inner jacket member 313. After the lower cushion sheet is in place, a section of the capillary bundle B is placed on the lower cushion sheet 321 in an arrangement wherein the capillary tubes are in a planar parallel array extending the length of the jacket members 313, 331 and side-by-side between the flanges 317 of the lower inner jacket member 313. As so positioned, the tubes are preferably evenly spaced and close together, if not in actual contact, out of contact with the flanges of the lower inner jacket member.

Figure 19:
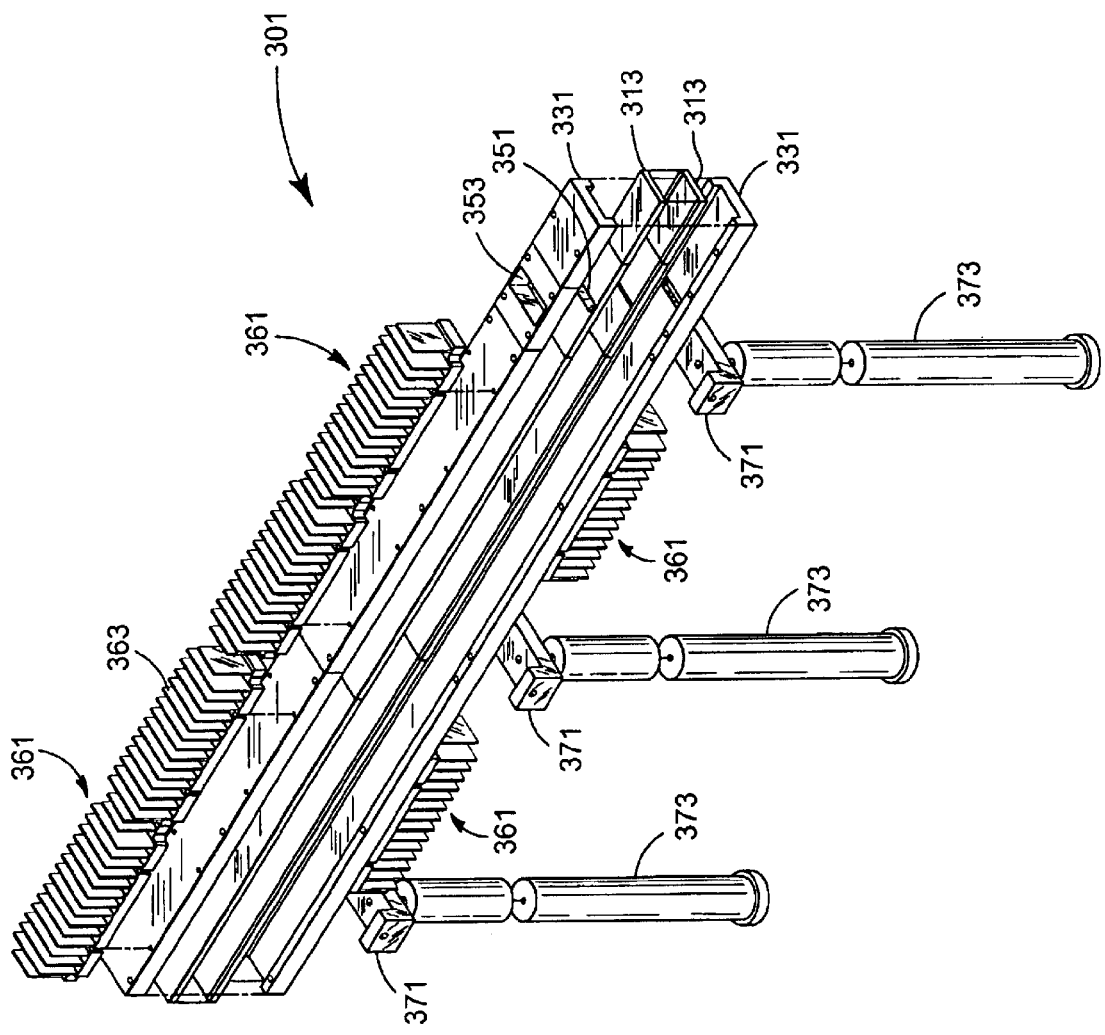
FIG. 19 is an exploded perspective showing certain components of the apparatus of FIG. 18.
Figure 20:
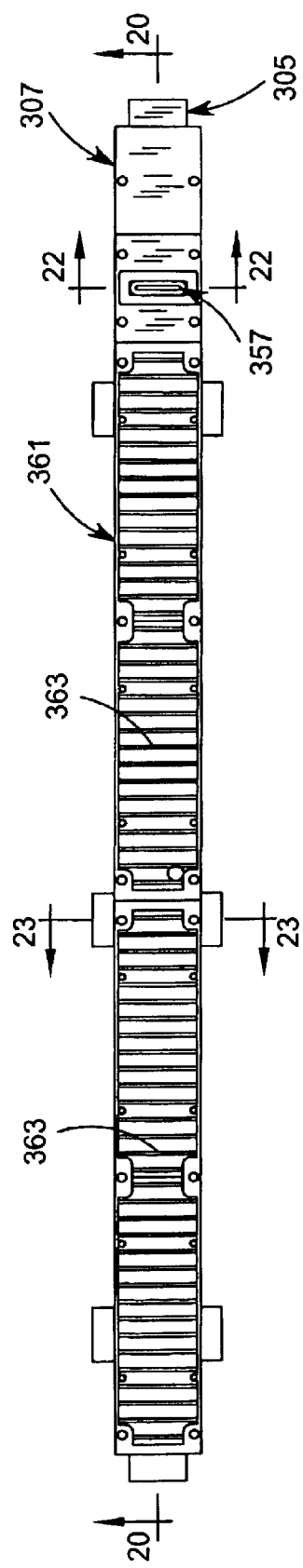
FIG. 20 is a top plan view of the apparatus of FIG. 18.

After the capillary tubes have been suitably arranged, the upper cushion sheet 321 and upper jacket components 313, 331 are assembled in similar fashion. That is, the upper cushion sheet 321 is placed on top of the bundle and a window opening 355 is cut (or pre-cut) in alignment with the lower window openings 351, 353. Alternatively, the cushion sheet 321 could be divided into two longitudinal sections spaced apart to define a window opening. The upper inner and upper outer jacket members 313, 331 are then placed in position, with the window openings 351, 353 aligned and the entire assembly secured by fasteners. If the upper inner and outer jacket members are each formed in multiple pieces, as shown in FIG. 19, the relatively short window piece of the inner jacket member 313 is preferably placed in position first, thus ensuring that the window opening 351 in this piece is properly aligned with the window openings below it, and that the tubes of the bundle are in the desired final position. Once this window piece is positioned, the other pieces of the inner jacket member 313 can be assembled end to end. The same procedure is followed using the pieces of the upper outer jacket member 331. Again, thermal grease may be used where appropriate.

The upper and lower jacket members 305 307 are secured together by suitable means, such as the threaded fasteners. The components of the jacket are sized and configured relative to one another so that when the jackets are secured in their closed position, the bundle B, cushion sheets 321, and inner and outer jackets 305, 309 are in close thermal contact with one another and, preferably, the bundle is subjected to a light compressive force to further enhance thermal conductivity for the efficient transfer of heat generated during a CE procedure from capillary tubes out through the cushion sheets and the jacket members for suitable dissipation. As noted above, this dissipation may be increased by the use of optional heat sinks 361. Besides providing excellent thermal conductivity, the inner jacket 305 functions to electrically insulate the bundle from the outer metal jacket 307. The cushion sheets 321 function to cushion the capillary tubes to prevent damage thereto when the jackets are secured in closed position.

After the jackets 305, 307 are secured in their closed positions, a CE procedure using high-voltages may be initiated in a conventional manner. The solid-state cooling apparatus of the present invention effectively cools the bundle B over a substantial length of the bundle while also electrically insulating the bundle to prevent the flow of current on the outside of the tubes. Further, since the tubes of the bundle are located inside the jackets, they are protected against damage and remain well organized.

It will be understood that the embodiments described above are intended to be illustrative only, and other embodiments are contemplated as falling within the scope of this invention. For example, it is contemplated that a solid-state cooling device of the present invention could comprise only a single jacket corresponding to the inner jacket 305 described above. In other words, the outer jacket 331 could be eliminated altogether. Further, the cushion 309 for protecting the capillary tubes could take many forms, and could even be eliminated entirely. Also, while the inner jacket members 313 and outer jacket members 331 are illustrated as being symmetric, non-symmetric parts can be used.

The specific dimensions of the jacket components will vary depending on the particular application, but generally speaking, the lengths of the inner jacket 305 and outer jacket 307 are preferably such as to enclose a major portion of the length of the bundle, and preferably as much of the length of the bundle as possible. Further, the thicknesses of the base 333 of each outer jacket member 331, the web 315 of each inner jacket member 313 and a cushion sheet 321 should be sufficient to achieve the objectives set forth above. In general, the temperature differential between the center of each capillary tube and the outer surfaces of the outer jacket members 331 should be no greater than about 10 degrees K, and the various material thicknesses and thermal conductivities should be selected accordingly. In one embodiment, for example, each outer jacket member 331 is of aluminum having a thermal conductivity of about 237 W/m-K and a base thickness of about 5 mm.; each inner jacket member 313 is of boron nitride having a thermal conductivity of about 15–50 W/m-K and a web thickness of about 5 mm.; and each cushion sheet 321 is of a silicone elastomer having a thermal conductivity of about 6 W/m-K and a thickness of about 0.3 mm. A typical capillary tube has an OD of about 150–375 microns and a thermal conductivity of about 1.5 W/m-K, a larger diameter tube being less fragile than a smaller diameter tube. It will be understood, therefore, that different combinations of materials and thicknesses can be used to stay within the preferred maximum temperature differential of 10 K.

To reduce the aforementioned temperature differential, the thickness of the jacket members 313, 331 can be reduced. However, the lower thickness limits for certain materials may be limited by their dielectric breakdown voltage. For boron nitride, for example, this value is 40–200 kV/mm. Thus, to provide proper electrical insulation at a voltage of 30 kV, a minimum thickness of 0.75 mm of BN is needed. As a practical matter, the lower limit of thickness may be determined by the fragility of the material. To replace BN with a different material, that material should possess the appropriate thermal conductivity and electrical insulation properties. As noted previously, one such material is aluminum nitride having a thermal conductivity of 100 W/m-K and a dielectric strength of 40 kV/mm. However, this material is significantly more expensive and harder to machine.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above constructions without departing from the scope of the invention, it is intended that all matter contained in the above description or shown in the accompanying drawings shall be interpreted as illustrative and not in a limiting sense.

What is claimed is:

1. Apparatus for cooling a bundle of capillary tubes to prevent overheating of the tubes during a parallel capillary electrophoresis procedure, said apparatus comprising
    an inner jacket of thermally conductive solid material comprising mating inner jacket members movable between an open position in which the inner jacket members are separated to allow placement of the bundle in the inner jacket and a closed position in which the inner jacket members are mated together and the bundle is disposed inside the inner jacket in thermally conductive relation with the inner jacket,
    an outer jacket of thermally conductive solid material around the inner jacket and in thermally conductive relation therewith, said outer jacket comprising mating outer jacket members movable between an open position in which the outer jacket members are separated and a closed position in which the outer jacket members are mated together around the inner jacket, and
    said mating inner and outer jacket members defining a window to permit the passage of light through the window and the capillary tubes of the bundle at the location of the window.

2. Apparatus as set forth in claim 1 further comprising a cushion of thermally conductive, cushioning material inside the inner jacket and in thermally conductive relation with the inner jacket for cushioning the bundle when the inner jacket members are in said closed position.

3. Apparatus as set forth in claim 2 further comprising fasteners for drawing the mating inner jacket members together and causing the cushion inside the inner jacket members to press against said bundle.

4. Apparatus as set forth in claim 1 wherein said inner jacket is of an electrically insulating material.

5. Apparatus as set forth in claim 4 wherein said inner jacket is of a ceramic-like material having a thermal conductivity in the range of about 5–50 W/m-K, and a dielectric strength in the range of about 20–400 kV/mm.

6. Apparatus as set forth in claim 5 wherein said inner jacket is of boron nitride.

7. Apparatus as set forth in claim 5 wherein said inner jacket members comprise a pair of opposing slabs, each slab having a generally channel shape and defining a recess therein.

8. Apparatus as set forth in claim 7 further comprising a cushion of thermally conductive, cushioning material disposed inside the recesses of said slabs for cushioning the bundle when the inner jacket members are in said closed position.

9. Apparatus as set forth in claim 8 wherein said cushion has a thermal conductivity in the range of about 3–9 W/m-K.

10. Apparatus as set forth in claim 8 further comprising fasteners for drawing the mating inner jacket members together and causing the cushion inside the inner jacket members to press against said bundle.

11. Apparatus as set forth in claim 1 wherein said inner jacket members have opposing surfaces coated with an electrically insulating material.

12. Apparatus as set forth in claim 1 wherein said inner and outer jackets are elongate for covering a major portion of the length of the bundle and have approximately equal lengths.

13. Apparatus as set forth in claim 12 wherein said outer jacket members have recesses therein for receiving respective inner jacket members.

14. Apparatus as set forth in claim 1 further comprising a heat sink on at least one of said mating outer jacket members.

15. A combination of the apparatus set forth in claim 1 and a bundle of capillary tubes inside the inner and outer jackets, said jackets extending over at least 50% of the overall length of the capillary bundle.

16. A combination of the apparatus set forth in claim 1 and a bundle of capillary tubes inside the inner jacket, said inner jacket extending over at least 50% of the overall length of the capillary bundle.

17. Apparatus for cooling a bundle of capillary tubes to prevent overheating of the tubes during a parallel capillary electrophoresis procedure, said apparatus comprising
    an inner jacket of thermally conductive, electrically insulating solid material comprising mating inner jacket members movable between an open position in which the inner jacket members are separated to allow placement of the bundle in the inner jacket and a closed position in which the inner jacket members are mated together and the bundle is disposed inside the inner jacket in thermally conductive relation with the inner jacket,
    an outer jacket of thermally conductive solid material comprising mating outer jacket members movable between an open position in which the outer jacket members are separated and a closed position in which the outer jacket members are mated together around the inner jacket and in thermally conductive relation therewith,
    a cushion of thermally conductive, cushioning material disposed inside the inner jacket for cushioning the bundle when the inner and outer jacket members are in said closed position, and
    said mating inner and outer jacket members defining a window for permitting the passage of light through the window and the tubes of the bundle at the location of the window.

18. Apparatus as set forth in claim 17 wherein said inner jacket is of a ceramic-like material having a thermal conductivity in the range of about 5–50 W/m-K and a dielectric strength in the range of about 20–400 kV/mm.

19. Apparatus as set forth in claim 18 wherein said inner jacket is of boron nitride.

20. Apparatus as set forth in claim 17 wherein said inner jacket comprises a pair of opposing channel-shaped slabs defining recesses for receiving said cushion therein.

21. Apparatus as set forth in claim 17 further comprising fasteners for drawing the mating outer and inner jacket members together and causing the cushion inside the inner jacket members to press against said bundle.

22. Apparatus as set forth in claim 17 wherein said inner and outer jackets are elongate for covering a major portion of the length of the bundle and have approximately equal lengths.

23. Apparatus as set forth in claim 17 further comprising a heat sink on at least one of said mating outer jacket members.

24. A combination of the apparatus set forth in claim 17 and a bundle of capillary tubes inside the inner and outer jackets, said jackets extending over at least 50% of the overall length of the capillary bundle.

25. Apparatus for cooling a bundle of capillary tubes to prevent overheating of the tubes during a parallel capillary electrophoresis procedure, said apparatus comprising an inner jacket of thermally conductive solid material comprising mating inner jacket members movable between an open position in which the inner jacket members are separated to allow placement of the bundle in the inner jacket and a closed position in which the inner jacket members are mated together and the bundle is disposed inside the inner jacket in thermally conductive relation with the inner jacket, an outer metal jacket around the inner jacket and in thermally conductive relation therewith, said outer jacket comprises mating outer jacket members having recesses therein for receiving respective inner jacket members, said outer jacket members being movable between an open position in which the outer jacket members are separated and a closed position in which the outer jacket members are mated together around the inner jacket with the inner jacket members received in respective recesses of the outer jacket members, said mating inner and outer jacket members defining a window to permit the passage of light through the window and the capillary tubes of the bundle at the location of the window, and wherein said inner and outer jackets are elongate for covering a major portion of the length of the bundle and having approximately equal lengths, and wherein said outer jacket members have window openings therein aligned with window openings in the inner jacket when the jackets are closed.

26. Apparatus for cooling a bundle of capillary tubes to prevent overheating of the tubes during a parallel capillary electrophoresis procedure, said apparatus comprising an inner jacket of thermally conductive, electrically insulating solid material comprising mating inner jacket members movable between an open position in which the inner jacket members are separated to allow placement of the bundle in the jacket and a closed position in which the inner jacket members are mated together and the bundle is disposed inside the inner jacket in thermally conductive relation with the inner jacket, an outer jacket of thermally conductive solid material comprising mating outer jacket members movable between an open position in which the jacket members are separated and a closed position in which the jacket members are mated together on opposite sides of the inner jacket and in thermally conductive relation therewith, a cushion of thermally conductive, cushioning material disposed inside the inner jacket for cushioning the bundle when the inner and outer jacket members are in said closed position, and a mechanism for moving the inner jacket members closer together to press the cushion against said bundle, said mating inner and outer jacket members defining a window for permitting the passage of light through the window and the tubes of the bundle at the location of the window.

27. Apparatus as set forth in claim 26 wherein said inner jacket members define a shallow recess extending between opposite ends of the inner jacket members for receiving said bundle of capillary tubes with the tubes arranged side-by-side in the recess with no intervening structure between the tubes.

28. Apparatus as set forth in claim 26 wherein said inner and outer jacket members are cooled without the aid of one or more thermoelectric devices.

29. Apparatus for cooling a bundle of capillary tubes to prevent overheating of the tubes during a parallel capillary electrophoresis procedure, said apparatus comprising an inner jacket of thermally conductive, electrically insulating solid material comprising mating inner jacket members movable between an open position in which the inner jacket members are separated to allow placement of the bundle in the jacket and a closed position in which the inner jacket members are mated together and define a shallow recess extending between opposite ends of the inner jacket members for receiving said bundle of capillary tubes with the tubes arranged side-by-side in the recess with no intervening structure between the tubes and with the tubes in thermally conductive relation with the inner jacket, an outer jacket of thermally conductive solid material comprising mating outer jacket members movable between an open position in which the jacket members are separated and a closed position in which the jacket members are mated together on opposite sides of the inner jacket and in thermally conductive relation therewith, and a cushion of thermally conductive, cushioning material disposed inside the inner jacket for cushioning the bundle when the inner and outer jacket members are in said closed position, said mating inner and outer jacket members defining a window for permitting the passage of light through the window and the tubes of the bundle at the location of the window.

* * * * *